(12) United States Patent
Ostafe et al.

(10) Patent No.: US 9,365,834 B2
(45) Date of Patent: Jun. 14, 2016

(54) GLUCOSE OXIDASE VARIANTS

(71) Applicant: Fraunhofer-Gesellschaft zur Foerderung der angewandten Forschung e.V, Munich (DE)

(72) Inventors: Raluca Ostafe, Aachen (DE); Radivoje Prodanovic, Belgrade (RS); Rainer Fischer, Aachen (DE)

(73) Assignee: Fraunhofer-Gesellschaft zur Förderung der angerwandten Forschung e. V., Munich (DE)

( * ) Notice: Subject to any disclaimer, the term of this patent is extended or adjusted under 35 U.S.C. 154(b) by 0 days.

(21) Appl. No.: 14/786,465

(22) PCT Filed: Apr. 17, 2014

(86) PCT No.: PCT/EP2014/057941
§ 371 (c)(1),
(2) Date: Oct. 22, 2015

(87) PCT Pub. No.: WO2014/173822
PCT Pub. Date: Oct. 30, 2014

(65) Prior Publication Data
US 2016/0068824 A1    Mar. 10, 2016

Related U.S. Application Data

(60) Provisional application No. 61/815,481, filed on Apr. 24, 2013.

(30) Foreign Application Priority Data

Apr. 24, 2013 (EP) .................................. 13165194

(51) Int. Cl.
*C12N 9/00* (2006.01)
*C12Q 1/54* (2006.01)
*C12N 9/04* (2006.01)

(52) U.S. Cl.
CPC ............... *C12N 9/0006* (2013.01); *C12Q 1/54* (2013.01); *C12Y 101/03004* (2013.01); *G01N 2333/902* (2013.01)

(58) Field of Classification Search
None
See application file for complete search history.

(56) References Cited

FOREIGN PATENT DOCUMENTS

| EP | 2562250 A1 | 2/2013 |
|---|---|---|
| WO | 03/072742 A2 | 9/2003 |
| WO | 2009104836 A1 | 8/2009 |
| WO | 2010121933 A1 | 10/2010 |
| WO | 2012017008 A1 | 2/2012 |
| WO | 2013026575 A2 | 2/2013 |

OTHER PUBLICATIONS

PCT/EP2014/057941 International Search Report mailed Nov. 6, 2014.
Davis et al. "Clinical Experience with a Glucose Oxidase-containing dressing on recalcitrant wounds." Journal of Wound Care, Mar. 1, 2009, 18(3):114-121.
Gueven et al. "Protein Engineering—An Option for Enzymatic Biofuel Cell Design." Electroanalysis, Apr. 2010, 22(7-8):765-775, VHC Publishers, Inc. USA.
Zhu et al. "Directed evolution of glucose oxidase from Aspergillus niger for ferrocenemethanol-mediated electron transfer." Biotechnology Journal, Feb. 2007, 2(2):241-248, Wiley-VCH Verlag, Germany.
Prodanovic et al. "Ultrahigh-throughput Screening System for Directed Glucose Oxidase Evolution in Yeast Cells." Combinatorial Chemistry and High Throughput Screening, Jan. 2011, 14(1):55-60, Bentham Science Publishers, NL.

*Primary Examiner* — Suzanne M Noakes
*Assistant Examiner* — Jae W Lee
(74) *Attorney, Agent, or Firm* — Wagenknecht IP Law Group PC

(57) ABSTRACT

The technology provided herein relates to novel variants of microbial glucose oxidase with improved properties, more specifically to polypeptides having glucose oxidase activity as their major enzymatic activity; to nucleic acid molecules encoding the glucose oxidases; vectors and host cells containing the nucleic acids and methods for producing the glucose oxidase; compositions comprising the glucose oxidase; methods for the preparation and production of such enzymes; and to methods for using such enzymes for food and feed processing, for the measurement of free glucose in clinical samples and bioreactors, and the development of miniature biofuel cells.

11 Claims, 2 Drawing Sheets

US 9,365,834 B2

GLUCOSE OXIDASE VARIANTS

CROSS-REFERENCE TO RELATED APPLICATIONS

This application is a U.S. National stage of PCT/EP2014/057941 filed on Apr. 17, 2014, which claims priority from U.S. Provisional Application Ser. No. 61/815,481 filed on Apr. 24, 2013 and EP Application Serial No. 13165194.5 filed on Apr. 24, 2013, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCT_EP2014_057941 SEQID" created on 20 Oct. 2015 and having a size of 51 Kilobytes. The sequence listing contained in this ASCII formatted document forms part of the specification and is herein incorporated by reference in its entirety.

FIELD OF THE DISCLOSURE

The technology provided herein relates to novel variants of microbial glucose oxidase with improved properties, more specifically to polypeptides having glucose oxidase activity as their major enzymatic activity; to nucleic acid molecules encoding said glucose oxidases; vectors and host cells containing the nucleic acids and methods for producing the glucose oxidase; compositions comprising said glucose oxidase; methods for the preparation and production of such enzymes; and to methods for using such enzymes for food and feed processing, for the measurement of free glucose in clinical samples and bioreactors, and the development of miniature biofuel cells.

BACKGROUND

Glucose oxidase (β-D-glucose:oxygen 1-oxidoreductase; EC 1.1.2.3.4) catalyzes the oxidation of β-D-glucose to gluconic acid, by utilizing molecular oxygen as an electron acceptor with the simultaneous production of hydrogen peroxide. Microbial glucose oxidase is currently receiving much attention due to its diverse applications in the chemical, pharmaceutical, food, beverage, clinical chemistry, biotechnology and other industries. Novel applications of glucose oxidase in biosensors have increased demand in recent years. Glucose oxidases have been isolated from various microbial sources.

The *Aspergillus niger* enzyme glucose oxidase is used e.g. in the food processing and pharmaceutical industries, and as a component of immunoassays and biosensors in the medical diagnostics field. The enzyme is also used to manufacture miniature biofuel cells that can power biomedical implants such as biosensors and insulin pumps. The output of these devices is limited by the performance of glucose oxidase within the anodic compartment.

In particular, three enzyme properties are relevant in the context of biofuel cells: (1) the rate of electron transfer from the electrode to the enzyme (the intrinsic enzyme activity); (2) the activity of the enzyme under physiological conditions (pH 7.4 and 5 mM glucose); and (3) the thermal stability of the enzyme.

WO89/126675 describes the production of glucose oxidase from *Aspergillus niger* in recombinant systems and WO 2008/079227 A1 relates to a obtained from *Aspergillus niger* formulated in a composition conferring improved storage stability. Glucose oxidases from different origins have also been disclosed including marine algae, e.g. *Chondrus crispus* (U.S. Pat. No. 7,544,795, U.S. Pat. No. 6,924,366), filamentous fungi, e.g. *Cladosporium* spp. (WO 95/29996, WO 1998/020136, U.S. Pat. No. 5,834,280) and *Talaromyces flavus* (U.S. Pat. No. 6,054,318). WO2012/017008 A1 discloses variants of *Aspergillus niger* glucose oxidase with altered enzymatic efficiency compared to the wild-type glucose oxidase.

However, the availability of glucose oxidases with improved properties for numerousness applications would be highly advantageous.

SUMMARY OF THE DISCLOSURE

The improved glucose oxidases according to the present disclosure may be used for such numerous applications, including the removal of oxygen from foods and beverages, the generation of hydrogen peroxide for food preservation, the measurement of free glucose in clinical samples and bioreactors, and the development of miniature biofuel cells. Many industrial processes could therefore benefit from using the improved variants of the glucose oxidases according to the present disclosure.

In a first aspect, embodiments of the disclosure provide polypeptides having glucose oxidase activity, wherein said polypeptide comprises variations at positions corresponding to the amino acid residues T30, I94 and A162 in the wild-type glucose oxidase from *Aspergillus niger* (SEQ ID NO: 1), and at least one or more further variations at positions corresponding to amino acid residues M556, R537, R37, V106, V293 or E310, and wherein the amino acid sequence of said polypeptide has at least a minimum percentage sequence identity and/or percentage homology of at least 80% to the amino acid sequence of SEQ ID NO. 1.

In a further aspect, embodiments of this disclosure relate to nucleic acid molecules, selected from the group consisting of
  a) a nucleic acid molecule encoding a polypeptide according to any one of claims 1 to 15;
  b) a nucleic acid molecule encoding for a polypeptide according to any one of claims 1 to 15 in which one or more amino acid residues are conservatively substituted;
  c) a nucleic acid molecule that is a fraction, variant, derivative, or fragment of the nucleic acid molecule presented as SEQ ID NO:6, SEQ ID NO:8, SEQ ID NO:10, SEQ ID NO:12 or SEQ ID NO:14;
  d) or a complement of any of the nucleic acid molecules of a)-c).

In a further aspect, embodiments of this disclosure relate to a vector comprising a nucleic acid molecule according to the present disclosure and to a host cell transformed, transduced or transfected with said vector.

In still another aspect, embodiments of this disclosure provide methods of producing a polypeptide having glucose oxidase activity comprising the steps of: (a) culturing a host cell according to the present disclosure in a suitable culture medium under suitable conditions to produce polypeptides having glucose oxidase activity; (b) obtaining said produced polypeptides, and optionally (c) processing the polypeptides.

In a further aspect, some embodiments of this disclosure relate to compositions comprising a polypeptide according to the present disclosure, in particular to food compositions, pharmaceutical compositions, diagnostic compositions and cosmetic compositions.

In still another aspect, some embodiments provide methods for assaying glucose in a sample, in which the sample is placed in contact with a polypeptide having glucose oxidase activity according to the present disclosure, and measuring the amount of the glucose oxidized by the glucose oxidase.

Further, some embodiments pertains to devices and kits for assaying glucose in a sample comprising a polypeptide having glucose oxidase activity according to the present disclosure and an electron mediator.

Furthermore, some embodiments relate to enzyme electrodes having a polypeptide with glucose oxidase activity according to the present disclosure that is immobilized on the electrode.

Further, some other embodiments pertain to enzyme sensors for assaying glucose comprising an enzyme electrode according the present disclosure as a working electrode.

In another aspect, embodiments relate to the use of a polypeptide having glucose oxidase activity according to the present disclosure for food processing.

In particular, in another aspect embodiments of the present disclosure pertains to modified glucose oxidases comprising substitutions of at least three amino acid residues in the amino acid sequence of the naturally occurring wild-type glucose oxidase from *Aspergillus niger* at positions corresponding to 556 and 537 or 37 relative to the numbering of the amino acid sequence of wild-type glucose oxidase from *Aspergillus niger* (SEQ ID NO: 1), and at least substitutions at positions corresponding to amino acid residues 556 and 537 or 37 and 106, and wherein said modified glucose oxidase has an increased intrinsic activity than the wild type enzyme.

Before the disclosure is described in detail, it is to be understood that this disclosure is not limited to the particular component parts of the devices described or process steps of the methods described as such devices and methods may vary. It is also to be understood that the terminology used herein is for the purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

DETAILED DESCRIPTION OF THE DISCLOSURE

Figure 1:
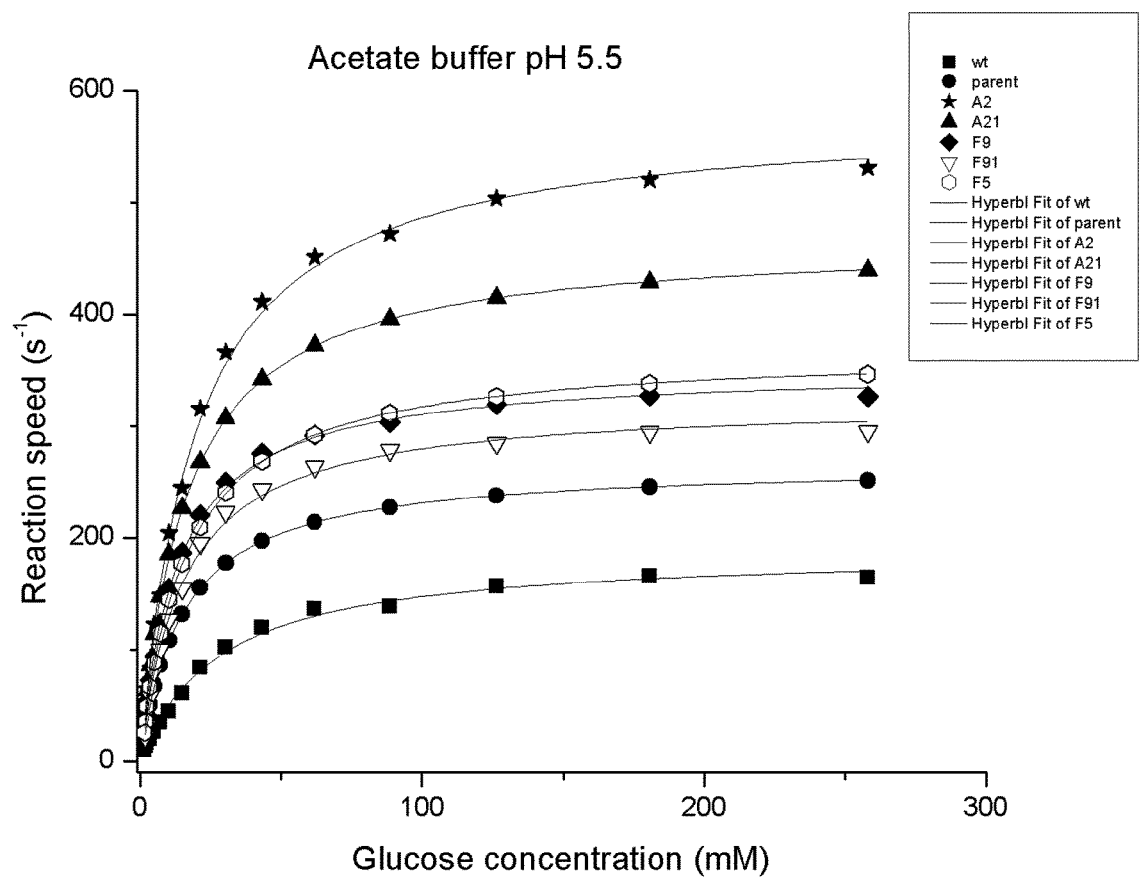
FIG. 1 is a diagram showing the enzyme kinetics of GOx variants according to the present disclosure at pH 5.5.

Disclosed herein are variants of the enzyme glucose oxidase (β-d-glucose:oxygen 1-oxidoreductase; EC 1.1.2.3.4), in particular of variants of the wild-type *Aspergillus niger* glucose oxidase comprising an amino acid sequence of SEQ ID NO: 1 and nucleic acid molecules encoding said glucose oxidase variants that may be used in industrial applications including food processing and pharmaceutical manufacturing, as well as a component of immunoassays and biosensors in the medical diagnostics field. The enzyme variants may also be used to manufacture miniature biofuel cells that can power biomedical implants such as biosensors and insulin pumps.

In particular, glucose oxidase variants according to the present disclosure show improved catalytic efficiency compared to the wild type and parent glucose oxidase and/or improved stability properties such as thermal stability and/or pH-stability. These characteristics make them specifically useful for industrial and diagnostic applications.

In general, the present disclosure pertains to polypeptides having glucose oxidase activity, wherein said polypeptides comprise variations at positions corresponding to the amino acid residues T30 and I94 in the wild-type glucose oxidase from *Aspergillus niger* (SEQ ID NO: 1), and at least one or more further variations at positions corresponding to amino acid residues M556, R537, R37, A162, V106, V293 or E310, and wherein the amino acid sequence of said polypeptides has at least a minimum percentage sequence identity of at least 80% to the amino acid sequence of SEQ ID NO. 1 or variants, modified forms, homologs, fusion proteins, functional equivalents and fragments thereof.

For example, a homologous polypeptide according to the present disclosure comprises any active glucose oxidase with a percentage sequence identity of at least 70% or preferably at least 80%, 85%, 90%, 95%, 97% or 99% to SEQ ID NO: 5, SEQ ID NO: 7, SEQ ID NO: 9, SEQ ID NO: 11 or SEQ ID NO: 13 and comprising variations at positions corresponding to the amino acid residues T30 and I94 and at least one or more further variations at positions corresponding to amino acid residues M556, R537, R37, A162, V106, V293 or E310.

The present disclosure reveals glucose oxidase enzymes with an amino-acid sequence derived from the amino acid sequence shown in SEQ ID NO:1 or variants, modified forms, homologs, fusion proteins, functional equivalents or functional fragments thereof, having variations at positions corresponding to the amino acid residues T30 and I94 and at one or more positions selected from the group of positions that correspond structurally or by amino acid sequence homology to the positions M556, R537, R37, A162, V106, V293 or E310.

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

The term "complementary" as used herein refers to a relationship between two nucleic acid sequences. One nucleic acid sequence is complementary to a second nucleic acid sequence if it is capable of forming a duplex with the second nucleic acid, wherein each residue of the duplex forms a guanosine-cytidine (G-C) or adenosine-thymidine (A-T) base pair or an equivalent base pair. Equivalent base pairs can include nucleoside or nucleotide analogues other than guanosine, cytidine, adenosine, or thymidine.

The phrase "a position corresponding to" as used herein means the position of an amino acid residue in a query amino acid sequence that is aligned with the amino acid residue in a reference amino acid sequence using a software AlignX of Vector NTI with default parameters (available from Invitrogen; see, Lu, G., and Moriyama, E. N. (2004) Vector NTI, a balanced all-in-one sequence analysis suite. Brief Bioinform 5, 378-88). Thus, "amino acid (AA) residue at a position corresponding to the position Y of the amino acid sequence set forth in SEQ ID NO: X" means the amino acid residue in a query amino acid sequence that is aligned with amino acid Y of SEQ ID NO: X when the query amino acid sequence is aligned with SEQ ID NO: X using AlignX of Vector NTI with default parameters. It should be noted that the amino acid Y of SEQ ID NO: X itself is also encompassed by this term. The mutant glucose oxidase of the present disclosure exhibit increased oxidase activity while substantially retaining and/or increasing enzyme stability, in particular thermo stability.

As used herein "activity" or "catalytic activity" describes quantitatively the conversion of a given substrate under defined reaction conditions. The term "residual activity" is defined as the ratio of the catalytic activity of the enzyme under a certain set of conditions to the catalytic activity under a different set of conditions. The term "specific activity" or "intrinsic activity" describes quantitatively the catalytic activity per amount of enzyme under defined reaction conditions. In particular, an oxidase activity describes the enzymatic activity of the glucose oxidase to catalyze oxidation of glucose to generate gluconolactone utilizing oxygen as an electron acceptor. For example, the oxidase activity may be assayed with the assays described in the examples of the present disclosure (see example 7). As mentioned the "activity" of a glucose oxidase as used herein may be directed to a measure of its ability to catalyze the oxidation reaction D-glucose+$O_2$→gluconolactone+$H_2O_2$ and may be expressed as the rate at which the product of the reaction is produced. For example glucose oxidase activity can be represented as the amount of product (gluconolactone and/or $H_2O_2$) produced per unit of time, or per unit (e.g. concentration or weight) of glucose oxidase.

The activity improved by the GOx variants according to the present disclosure are in particular the instrinsic activity (specific activity) but also the activity in general. As used herein "$K_{cat}$" means reaction speed at high concentrations of substrate (saturating conditions) divided by the concentration of enzyme (per enzyme unit). "$K_m$" is defined as the concentration of substrate at which the enzyme reaches maximum speed but it relates to the speed of the reaction at non-saturating substrate conditions so at low glucose concentration. "$K_{cat}/k_m$" is the specificity constant and sums up the 2 properties. In advantageous embodiments, all the improved GOx variants according to the present disclosure show improved $k_{cat}$ and a better km (and therefore the $k_{cat}/k_m$) compared to the wild type variant The term "enzyme" in accordance with the invention means any substance composed wholly or largely of protein or polypeptides that catalyzes or promotes, more or less specifically, one or more chemical or biochemical reactions. The term "enzyme" can also refer to a catalytic polynucleotide (e.g. RNA or DNA).

The term "oxidation reaction" means in general terms a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. As mentioned above, glucose oxidase typically catalyzes the oxidation of a primary alcohol group to an aldehyde.

The term "glucose oxidase" or "GOx" specifies a protein that catalyzes the oxidation of beta-D-glucose into D-glucono-1,5-lactone (D-glucose+$O_2$→gluconolactone+$H_2O_2$), which then may hydrolyze to gluconic acid. Accordingly, the glucose oxidase is an enzyme. Further, the term "a polypeptide having the activity of a glucose oxidase" refers to a polypeptide having the before mentioned activity. The enzyme glucose oxidase is thus a member of the class of oxidation enzymes that catalyzes an oxidation reaction, by adding, inserting, contributing or transferring oxygen from a source or donor to a substrate. Such enzymes are also called oxidoreductases or redox enzymes, and encompass oxygenases, hydrogenases or reductases, oxidases and peroxidases. In this regard, the terms "oxygen donor", "oxidizing agent" and "oxidant" mean a substance, molecule or compound which donates oxygen to a substrate in an oxidation reaction. Typically, the oxygen donor is reduced (accepts electrons). Examples of oxygen donors, which are not limiting, include molecular oxygen or dioxygen ($O_2$) and peroxides, including alkyl peroxides such as t-butyl peroxide, and most preferably hydrogen peroxide ($H_2O_2$). A peroxide is any compound having two oxygen atoms bound to each other.

The nucleic acid molecule according to the present disclosure encodes a polypeptide or fragment thereof which is derived from glucose oxidase (GOx) from *Aspergillus niger* (SEQ ID NO: 1) with improved kinetic properties and/or stability, in particular thermo stability of the enzyme in the reaction from glucose to gluconolactone and $H_2O_2$. Glucose oxidase from *Aspergillus niger* is a well-characterized protein forming a dimer, 160 kDa in size and crystal structures have been solved (Hecht H J et al. Crystal structure of glucose oxidase from *Aspergillus niger* refined at 2.3 Angstrom resolution. Journal of Molecular Biology 1993: 229(1)153-172).

The term "glucose oxidase variants", "modified glucose oxidase" or "glucose oxidase mutant" means any glucose oxidase obtained e.g. by site-directed or random mutagenesis, insertion, deletion, recombination and/or any other protein engineering method, which leads to a glucose oxidase that differs in amino acid sequence from the corresponding wild type glucose oxidase. The terms "wild type glucose oxidase", "wild type enzyme", or "wild type" in accordance with the disclosure describe a glucose oxidase enzyme with an amino acid sequence found in nature or a fragment thereof.

The term "parental glucose oxidase", "parent" or "parent GOx" as used herein means a glucose oxidase comprising the amino acid sequence of SEQ ID NO: 3 (with the substitutions at positions corresponding to the amino acid residues T30V, I94V and A162T of the wild-type glucose oxidase from *Aspergillus niger* (SEQ ID NO: 1) or a glucose oxidase comprising the amino acid sequence of SEQ ID NO: 1 with the substitutions at positions corresponding to the amino acid residues T30V and I94V.

The term "derivative" as used herein, refers to a nucleic acid molecule that has similar binding characteristics to a target nucleic acid sequence as a nucleic acid molecule according to one of the claimed sequences.

The term "expression clone" refers to DNA sequences containing a desired coding sequence and control sequences in operable linkage, so that hosts transformed with these sequences are capable of producing the encoded proteins. The term "expression system" refers to a host transformed with an expression clone. To effect transformation, the expression clone may be included on a vector; however, the relevant DNA may also be integrated into the host chromosome.

The term "fusion proteins" comprises all proteins derived from a modified glucose oxidase according to the present disclosure by covalently fusing additional amino acid sequences at the C- and/or N-terminus. The source and composition of the additional amino acid sequence is either natural from any living organism or virus, or unnatural. In particular, the fusion protein may be a "recombinant" polypeptide, which is defined either by its method of production or its structure. In reference to its method of production, recombinant polypeptides are made by a process involving the use of recombinant nucleic acid techniques. In reference to structure, recombinant polynucleotides or polypeptides contain sequences from different sources. In particular, it encompasses polypeptides made by generating a sequence comprising two or more fragments, which are not naturally contiguous or operably linked to each other. Thus, for example, products made by transforming cells with any unnaturally occurring vector are encompassed.

The term "functional fragment" or "effective fragment" means a fragment or portion of a glucose oxidase variant according to the present disclosure that retains approximately the same improved enzymatic function or effect and/or the same thermo stability.

The term "gene" refers to a DNA sequence that comprises control and coding sequences necessary for the production of a recoverable bioactive polypeptide or precursor.

The term "homologous polypeptide" or "homolog" according to the present disclosure comprises any enzyme with a sequence identity of at least 70% or preferably at least 80%, 85%, 90%, 95%, 97% or 99% to a glucose oxidase variant according to the present disclosure including functional fragments or effective fragments thereof.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same enzymatic and/or stability properties as the latter.

The term "host cell" in relation to the present disclosure includes any cell that comprises either the nucleic acid molecule or an expression vector as described above and which is used in the heterologous production of an enzyme having the specific properties as defined herein or in the methods of the present disclosure.

The term "isolated" describes any molecule separated from its natural source.

The term "modified form" or "variant" means that the enzyme has been modified from its original form (parent/wild-type, wt) but retains at least the same enzymatic functional characteristics as that of the wild-type enzyme.

The term "modification" or "variation" as used herein, refers for example to substitutions, insertions or deletions of amino acid residues at specific positions in an amino acid sequence as well as the phosphorylation, acetylation, palmitoylation, methylation, sulphation, glycosylation, lipidation, isoprenylation, farnesylation, attachment of a fatty acid moiety, glypiation and/or ubiquitinylation of specific positions on the polypeptide, or combinations thereof. In an advantageous embodiment, the variation is a substitution.

The term "mutation" refers to the substitution or replacement of single or multiple nucleotides, insertions or deletions of one or more triplets/codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above-described changes. Amino acid residues are abbreviated according to the following Table 1 either in one- or in three-letter code.

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The term "oligonucleotide" as used herein is defined as a molecule comprised of two or more deoxyribonucleotides or ribonucleotides. The exact size will depend on many factors, which in turn depends on the ultimate function or use of the oligonucleotide. Oligonucleotides can be prepared by any suitable method, including, for example, cloning and restriction of appropriate sequences and direct chemical synthesis by a method such as the phosphotriester method, the diethylphosphoramidite method, and the solid support method. A review of synthesis methods is provided in Goodchild J, Bioconjug. Chem. (1990) 165-187.

The term "plasmid", "vector system", "vector" or "expression vector" means a construct capable of in vivo or in vitro expression. In the context of the present disclosure, these constructs may be used to introduce genes encoding enzymes into host cells.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff et., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (www.ncbi.nlm.nih.gov/).

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "position" in a polynucleotide or polypeptide refers to specific single bases or amino acid residues in the sequence of the polynucleotide or polypeptide, respectively.

The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide.

The term "thermo stable enzyme", "thermo stable glucose oxidase" or "thermo stable polypeptide", as used herein, refers to an enzyme that is stable to heat and has maintained high activity after exposure to an elevated temperature. The "thermal stability" or "thermo stability" of the glucose oxidase mutants or variants according to the present disclosure was determined by incubating the enzyme in 50 mM acetate buffer (pH 5.5) at 60° C. in the absence of substrate and measuring the residual activity of periodic aliquots using the ABTS assay (see example 8).

The term "variant of the nucleic acid molecule" refers herein to a nucleic acid molecule which is substantially similar in structure and biological activity to a nucleic acid molecule according to one of the claimed sequences.

TABLE 1

Amino acid abbreviations

| Abbreviations | | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Mutations or variations are described by use of the following nomenclature: position; substituted amino acid residue(s). According to this nomenclature, the substitution of, for instance, an alanine residue for a glycine residue at position 20 is indicated as 20G. When an amino acid residue at a given position is substituted with two or more alternative amino acid residues these residues are separated by a comma or a slash. For example, substitution of alanine at position 20 with either glycine or glutamic acid is indicated as 20G/E, or 20G, 20E.

Furthermore, the following nomenclature could also be used: amino acid residue in the protein scaffold; position; substituted amino acid residue(s). According to this nomenclature, the substitution of, for instance, an alanine residue for a glycine residue at position 20 is indicated as Ala20Gly or A20G, or 20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as Δ(Ala20-Gly21) or Δ(A20-G21). When a sequence contains a deletion in comparison to the parent protein used for numbering, an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below that describes a generally accepted Venn diagram grouping of amino acids.

TABLE 2

Venn diagram grouping amino acids

| Set | | Sub-set | |
|---|---|---|---|
| Hydrophobic | F W Y H K M I L V A G C | Aromatic Aliphatic | F W Y H I L V |
| Polar | W Y H K R E D C S T N Q | Charged Positively charged Negatively charged | H K R E D H K R E D |
| Small | V C A G S P T N D | Tiny | A G S |

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These posttranslational modifications may or may not have an influence on the physical or enzymatic properties of the enzymes as explored herein.

As mentioned above, the present disclosure pertains to a polypeptide having glucose oxidase activity, wherein said polypeptide comprises variations at positions corresponding to the amino acid residues T30 and I94 in the wild-type glucose oxidase from *Aspergillus niger* (SEQ ID NO: 1), and at least one or more further variations at positions corresponding to amino acid residues M556, R537, R37, A162, V106, V293 or E310, and wherein the amino acid sequence of said polypeptide has at least a minimum percentage sequence identity of at least 80% to the amino acid sequence of SEQ ID NO. 1.

In advantageous embodiments, said polypeptide comprises at least variations at positions corresponding to amino acid residues T30, I94, A162 and at least one or more variations at positions corresponding to amino acid residues M556, R537, R37, V106, V293 or E310 of the amino acid sequence set forth in SEQ ID NO: 1.

In another embodiment, said polypeptide comprises at least variations at positions corresponding to amino acid residues T30, I94, A162 and at least a variation at amino acid residue M556, in particular in combination with at least a variation at a position corresponding to amino acid residue R537 of the amino acid sequence set forth in SEQ ID NO: 1.

In advantageous embodiments, said polypeptide comprises at least variations at positions corresponding to amino acid residues T30, I94, A162 and at least a variation at position corresponding to the amino acid residue R37, in particular with a combination of at least a variation at a position corresponding to amino acid residues R37 and V106 of the amino acid sequence set forth in SEQ ID NO: 1.

In advantageous embodiments, said polypeptide comprises at least variations at positions corresponding to amino acid residues T30, I94, A162 and at least a variation at position corresponding to the amino acid residue V106 and/or at least a variation at a position corresponding to the amino acid residue V293 of the amino acid sequence set forth in SEQ ID NO: 1.

In advantageous embodiments, said polypeptide comprises at least variations at positions corresponding to amino acid residues T30, I94, A162 and at least a variation at position corresponding to the amino acid residue E310 of the amino acid sequence set forth in SEQ ID NO: 1.

In before mentioned glucose oxidase mutants according to the present disclosure, said variations are substitutions selected from the group T30V, I94V, R37K, V106I, A162T, V293I, E310, R537K and M556V, or combinations thereof.

Preferred examples of the polypeptide having improved glucose oxidase activity compared to the wild type enzyme comprises the substitutions selected from the group consisting of:
a) M556V, R537K, T30V, I94V
b) M556V, R537K, T30V, I94V, A162T
c) M556V, R537K, R37K, V293I, E310D, T30V, I94V, A162T
d) M556V, R37K, V106I, T30V, I94V, A162T
e) R37K, V106I, T30V, I94V, A162T Table 3 shows a list of advantageous mutant glucose oxidase variants according to the present disclosure, comprising variations at positions corresponding to the amino acid residues of the amino acid sequence set forth in SEQ ID NO: 1.

TABLE 3

Advantageous substitutions in SEQ ID NO: 1

| Mutant name | T30V | R37K | I94V | V106I | A162T | V293I | E310D | R537K | M556V |
|---|---|---|---|---|---|---|---|---|---|
| Parent | x | | x | | x | | | | |
| A21 | x | | x | | | | | x | x |
| A2 | x | | x | | x | | | x | x |
| F5 | x | x | x | | x | x | x | x | x |
| F91 | x | x | x | x | x | | | | |
| F9 | x | x | x | x | x | | | | x |

An advantageous embodiment of the disclosure pertains to a polypeptide having glucose oxidase activity comprising an amino acid sequence selecting from the group consisting of SEQ ID NO: 5, SEQ ID NO: 7, SEQ ID NO: 9, SEQ ID NO: 11 or SEQ ID NO: 13, in particular to a polypeptide comprising the amino acid sequence of SEQ ID NO: 7 or SEQ ID NO: 11, wherein the polypeptide has improved glucose oxidase activity ($k_M$, $k_{ca\ and/or}\ k_{cat}/k_M$) and/or improved thermo stability in view of the wild-type enzyme and to the parent GOx.

In advantageous embodiments the polypeptides having glucose oxidase activity according to the present disclosure have at least 1.2, at least 1.4, at least 1.5, at least 1.6, or at least 1.7 fold increase in activity at pH 5.5 than the parental GOx and/or at least 1.2, at least 1.4 at least 1.5, at least 1.6 or at least 1.7 increase in activity at pH 5.5 than the parental GOx.

In another advantageous embodiments the polypeptides having glucose oxidase activity according to the present disclosure have at least 3, at least 3.5 and at least 4 fold increase in activity at pH 5.5 than the wild-type GOx and/or at least 2.5, at least 3, at least 4, at least 5 or at least 5.8 fold increase in activity at pH 7.4 than the wild-type GOx.

The present disclosure pertains also to polypeptides comprising the above mentioned variations, in particular substitutions of an amino acid sequence with a at least a minimum percentage sequence identity of 85%, at least 90%, at least 93%, at least 96%, at least 97%, at least 98% or at least 99% to the amino acid sequence of SEQ ID NO. 1.

Embodiments of this disclosure also include variants of any of the glucose oxidases set forth in SEQ ID NO: 5, SEQ ID NO: 7, SEQ ID NO: 9, SEQ ID NO: 11 or SEQ ID NO: 13, in particular to a polypeptide comprising the amino acid sequence of SEQ ID NO: 7 or SEQ ID NO: 11, which have glucose oxidase activity and an amino acid sequence having a percent sequence identity of at least 50%, at least 60%, at least 75%, at least 80%, at least 85%, at least 90%, at least 93%, at least 95%, at least 96%, at least 97%, at least 98%, and at least 99% as compared to each of the glucose oxidase variants set forth in sequences SEQ ID NO: 5, SEQ ID NO: 7, SEQ ID NO: 9, SEQ ID NO: 11 or SEQ ID NO: 13.

Further embodiments of the disclosure are nucleic acid molecules, selected from the group consisting of
- e) a nucleic acid molecule encoding a polypeptide according to the present disclosure;
- f) a nucleic acid molecule encoding for a polypeptide according to the present disclosure in which one or more amino acid residues are conservatively substituted;
- g) a nucleic acid molecule that is a variant, homologue, derivative or fragment of the nucleic acid molecule presented as SEQ ID NO:6, SEQ ID NO:8, SEQ ID NO:10, SEQ ID NO:12 or SEQ ID NO:14;
- h) a nucleic acid molecule that is capable of hybridizing to any of the nucleic acid molecules of a)-c) under stringent conditions;
- i) a nucleic acid molecule that is capable of hybridizing to the complement of any of the nucleic acid molecules of a)-d) under stringent conditions;
- j) a nucleic acid molecule having a sequence identity of at least 95% with any of the nucleic acid molecules of a)-e) and encoding for a polypeptide having improved glucose oxidase activity and/or thermo stability;
- k) a nucleic acid molecule having a sequence identity of at least 85% with any of the nucleic acid molecules of a)-e) and encoding for a polypeptide having improved glucose oxidase activity and/or thermo stability;
- l) or a complement of any of the nucleic acid molecules of a)-g).

In one embodiment of the present disclosure, the glucose oxidase enzymes show particularly improved thermal stability and at the same time improved or retained intrinsic activity compared to the wild type GOx or the parental GOx enzyme. These characteristics make them specifically useful for food processing and other industrial or diagnostic applications.

Further embodiments of the disclosure are vectors, expression clones and host cells comprising nucleic acid molecules encoding the glucose oxidase variants according to the present disclosure.

Further embodiments are methods for preparing the glucose oxidase variants according to the present disclosure, which comprises culturing the transformed, transduced or transfected host cell and isolating the modified glucose oxidase from the culture.

Thus, the present disclosure also encompasses a vector comprising the polynucleotide encoding the mutant glucose oxidase, a host cell transformed with such a vector, and a method for preparing the mutant glucose oxidase of the invention by culturing the transformant, collecting and purifying the mutant glucose oxidase from the culture.

The disclosure also encompasses a method for assaying glucose in a by placing the glucose oxidase of the disclosure in contact with the sample and measuring the amount of the glucose oxidized by the glucose oxidase. In another aspect, the present disclosure provides a device for assaying glucose in a sample comprising the glucose oxidase of the disclosure and an electron mediator.

The assay device may have a similar structure as any of conventional, commercially available amperometric biosensor test strips for monitoring the blood glucose level. One example of such a device has two electrodes (working electrode and reference or counter electrode) positioned on an insulating substrate, a reagent port and a sample receiver. The reagent port contains the mutated glucose oxidase of the disclosure and a mediator. When a sample such as blood sample is added to the sample receiver, glucose contained in the sample will react with glucose oxidase to generate current, which is indicative of the amount of glucose in the sample. Typical examples of electrochemical sensors suited for the determination of enzyme substrates are known, e.g. from WO 2004/113900 and U.S. Pat. No. 5,997,817. As an alternative to electrochemical sensors, optical detection technologies might be used. Typically, such optical devices are based on color changes that occur in a reagent system comprising the enzyme, an electron mediator and an indicator. The color changes can be quantified using fluorescence, absorption or remission measurements. Typical examples of optical devices suited for the determination of enzyme substrates are known, e.g. from U.S. Pat. No. 7,008,799, U.S. Pat. No. 6,036,919, and U.S. Pat. No. 5,334,508.

In yet another aspect, the present disclosure provides a kit for assaying glucose in a sample comprising the glucose oxidase of the disclosure and an electron mediator.

A kit for the measurement of glucose may be constructed using the enzyme of the present disclosure. In addition to the glucose oxidase of the disclosure, the kit contains buffer necessary for the measurement, appropriate mediator and, if necessary, enzymes such as peroxidase, standard solution of glucose for the preparation of a calibration curve and an instruction for use. The glucose oxidase of the present invention may be provided in various forms, for example, as a freeze-dried reagent or as a solution in an appropriate storage solution.

In another aspect, the present invention provides an enzyme electrode having the glucose oxidase of the invention that is immobilized on the electrode.

In another aspect, the present disclosure provides an enzyme sensor for assaying glucose comprising the enzyme electrode of the disclosure as a working electrode. In an advantageous embodiment, the sensor is a disposable sensor.

The concentration of the glucose in a sample may be determined by measuring the amount of electrons generated by the enzyme reaction. Various sensor systems have been described in the art, including systems based on a carbon electrode, metal electrode, and platinum electrode. The mutated glucose oxidase of the present disclosure is immobilized on the electrodes. Examples of the means for immobilization include cross-linking, encapsulating into a macromolecular matrix, coating with a dialysis membrane, optical cross-linking polymer, electroconductive polymer, oxidation-reduction polymer, and any combination thereof.

When measurement is conducted in an amperometric system using carbon electrode, gold electrode or platinum electrode provided with an immobilized enzyme, it is used as a working electrode, together with a counter electrode (such as a platinum electrode) and a reference electrode (such as a Ag/AgCl electrode). The electrodes are inserted into a buffer containing a mediator and kept at a predetermined temperature. A predetermined voltage is applied to the working electrode, then a sample is added and the increased electric current is measured. Examples of the mediator used in the assay include potassium ferricyanide, ferrocene, osmium derivatives, ruthenium derivatives, phenazine methosulfate, nitrosoaniline derivates etc. It is generally also possible to use so-called two-electrode systems with one working electrode and one counter or pseudo-reference electrode.

Further, glucose may be assayed using an immobilized electron mediator in an amperometric system using a carbon electrode, gold electrode, or platinum electrode. The enzyme is immobilized on the electrode together with an electron mediator (such as potassium ferricyanide, ferrocene, an osmium derivative, or phenazine methosulfate) in a macromolecular matrix by means of adsorption or covalent binding to prepare a working electrode. It is inserted into buffer together with a counter electrode (such as a platinum electrode) and a reference electrode (such as a Ag/AgCl electrode), and kept at a predetermined temperature. A predetermined voltage is applied to the working electrode, then the sample is added and the increased electric current is measured.

As mentioned above, one embodiment of the present disclosure pertains to methods for producing a polypeptide having glucose oxidase activity comprising the steps of: (a) culturing a host cell comprising nucleic acid molecules encoding the glucose oxidase variants according to the present disclosure in a suitable culture medium under suitable conditions to produce polypeptides having glucose oxidase activity; (b) obtaining said produced polypeptides, and optionally (c) processing the polypeptides.

In order to produce the glucose oxidase enzyme, the DNA encoding the enzyme can be chemically synthesized from published sequences or obtained directly from host cells harboring the gene (e.g., by cDNA library screening or PCR amplification). The glucose oxidase gene can be included in an expression cassette and/or cloned into a suitable expression vector by standard molecular cloning techniques. Such expression cassettes or vectors often contain sequences that assist initiation and termination of transcription (e.g., promoters and terminators), and may contain selectable markers. Cassettes can also be comprised of plus or minus strand mRNA, and their expression may or may not include an amplification step before translation of the mRNA. The glucose oxidase gene to be expressed can contain or not contain certain domains of the protein, such as polymer binding domains (e.g., carbohydrate binding domains) of various specificities. The expression cassette or vector can be introduced in a suitable expression host cell which will then express the corresponding glucose oxidase gene. Particularly suitable expression hosts are bacterial expression host genera including *Escherichia* (e.g. *E. coli*), *Pseudomonas* (e.g. *P. fluorescens* or *P. stutzeri*), *Proteus* (e.g. *Proteus mirabilis*), *Ralstonia* (e.g. *R. eutropha*), *Streptomyces, Staphylococcus* (e.g. *S. carnosus*), *Lactococcus* (e.g. *L. lactis*), and *Bacillus* (e.g. *B. subtilis, B. megaterium, B. licheniformis*) Also particularly suitable are yeast expression hosts such as *Saccharomyces cerevisiae, Schizosaccharomyces pombe, Yarrowia lipolytica, Hansenula polymorpha, Kluyveromyces lactis* or *Pichia pastoris*. Especially suited are fungal expression hosts such as *Chrysosporium lucknowense, Aspergillus* (e.g. *A. oryzae, A. niger, A. nidulans*) or *Trichoderma reesei*. Also suited are mammalian expression hosts such as mouse (e.g. NS0), Chinese hamster ovary (CHO) or baby hamster kidney (BHK) cell lines, transgenic mammalian systems such as rabbit, goat or cattle, other eukaryotic hosts such as insect cells or plants, or viral expression systems such as bacteriophages M13, T7 or lambda, or eukaryote viruses such as Baculovirus.

Glucose oxidase genes can be introduced into the expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g. of host-cell protoplasts), biolistic "gene gun" transformation, PEG-mediated transformation (e.g. of host-cell protoplasts), protoplast fusion (e.g. using bacterial or eukaryotic protoplasts), liposome-mediated transformation, *Agrobacterium tumefaciens*, adenovirus or other viral or phage transformation or transduction.

The protein of interest can be secreted into the extracellular or periplasmic space or expressed intracellularly. Optionally, after intracellular expression of the enzyme variants, or secretion into the periplasmic space using signal sequences such as those mentioned above, a permeabilisation or lysis step can be used to release the glucose oxidase enzyme into the supernatant. The disruption of the membrane barrier can be effected by the use of mechanical means such as ultrasonic waves, pressure treatment (French press), cavitation or the use of membrane-digesting enzymes such as lysozyme or enzyme mixtures. As a further alternative, the genes encoding the glucose oxidase enzyme are expressed cell-free by the use of a suitable cell-free expression system. For example, the S30 extract from *Escherichia coli* cells was used for this purpose or commercially available systems (e.g. CECF technology by Roche Applied Science, Inc.). In cell-free systems, the gene of interest was typically transcribed with the assistance of a promoter, but ligation to form a circular expression vector is optional. RNA can also be exogenously added or generated without transcription and translated in cell free systems. Configurations of expression constructs for in vitro expression and execution of all of the above expression systems are well within the ability of the skilled artisan.

As described above, the glucose oxidase proteins can be expressed in a variety of expression systems and accordingly the appropriate downstream processing and purification procedures have to be selected. In an advantageous embodiment of the disclosure the glucose oxidase variant is expressed in a microbial host and the protein is secreted into the periplasmic or extracellular space. Cells expressing the glucose oxidase variants are preserved by methods well known to anyone skilled in the art, such as, but not limited, to cryo stocks. Cultures of the expressing organism are prepared at an appropriate volume with standard methods of fermentation. In a preferred embodiment, cultures for protein expression are inoculated from a cryo stock and the volume of the culture increased successively in the appropriate containers. In a preferred embodiment the cells are grown in a fermenter and optionally growth conditions such as pH, temperature, oxygen and/or nutrient supply are controlled. A first step of purification comprises the separation of cells from supernatant using one or more of several techniques, such as sedimentation, microfiltration, centrifugation, or flocculation. In a preferred embodiment the method applied is microfiltration. In case of intracellular expression the cells are subjected to treatments that result in a release of the protein from the intracellular space. These treatments may comprise for example pressure, enzymatic, osmotic shock, freezing, ultrasonic or other treatment to produce a cellular extract, which may or may not be subjected to further purification.

In an advantageous embodiment of the disclosure the protein is secreted into the supernatant and an optional step of purification comprises the concentration of the supernatant by ultrafiltration. Further protein purification from the supernatant or concentrated supernatant may be performed with one or more of several methods comprising extraction or fractionation methods such as ammonium sulfate or ethanol or acid precipitation, or chromatographic methods including but not limited to ion-exchange, hydrophobic interaction, hydroxylapatite, size fractionation by gel-filtration, phosphocellulose or lectin chromatography and affinity chromatography or any combination thereof. In a more preferred method the affinity-tagged protein is purified by metal-chelate affinity chromatography to obtain a high purity protein.

In another advantageous embodiment of the disclosure the supernatant or the supernatant partially purified by ultrafiltration or the concentrated and/or diafiltrated supernatant is dried by any one of several technical methods such as, but not limited to, spray-drying, lyophilisation, down-draught evaporation, thin-layer evaporation, centrifugal evaporation, conveyer drying or any combination thereof.

In a further advantageous embodiment of the disclosure the fermented cell-suspension including the expressed glucose oxidase variants is dried as a whole using processes such as, but not limited to, fluidized bed drying, conveyer drying, spray drying or drum drying or any combination thereof.

The polypeptide of interest that is produced may be recovered, further purified, isolated, processed and/or modified by methods known in the art. For example, the polypeptide may be recovered from the nutrient medium by conventional procedures including, but not limited to, centrifugation, filtration, ultrafiltration, extraction or precipitation. Further processing steps such as purification steps may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction. Furthermore, the isolated and purified polypeptide of interest may be further processed, e.g. formulated, into a composition, in particular to a food composition, a pharmaceutical composition, a diagnostic composition or a cosmetic composition.

In the following a sequence alignment of the amino acid sequences encoding wild-type glucose oxidase of *Aspergillus niger* (SEQ ID NO. 1) indicated as wt (top row), the parent glucose oxidase (SEQ ID NO. 3), indicated as having the substitutions T30V-I94V-A162T, the glucose oxidase variant of the present disclosure A21 (SEQ ID NO. 5) indicated as having the substitutions T30V-I94V-R537K-M556V, the glucose oxidase variant of the present disclosure A2 (SEQ ID NO. 7) indicated as having the substitutions T30V-I94V-A162T-R537K-M556V, the glucose oxidase variant of the present disclosure F5 (SEQ ID NO. 9) indicated as having the substitutions T30V-R37K-I94V-A162T-V293I-E310D-R537K-M556V, the glucose oxidase variant of the present disclosure F91 (SEQ ID NO. 11) indicated as having the substitutions T30V-R37K-I94V-V106I-A162T, and the glucose oxidase variant of the present disclosure F9 (SEQ ID NO. 13) indicated as having the substitutions T30V-R37K-I94V-V106I-A162T-M556V.

```
                                             60         70         80         90        100
wt         SNGIEASLLT DPKDVSGRTV DYIIAGGGLT GLTTAARLTE NPNISVLVIE
parent     SNGIEASLLT DPKDVSGRTV DYIIAGGGLV GLTTAARLTE NPNISVLVIE
A21        SNGIEASLLT DPKDVSGRTV DYIIAGGGLV GLTTAARLTE NPNISVLVIE
A2         SNGIEASLLT DPKDVSGRTV DYIIAGGGLV GLTTAARLTE NPNISVLVIE
F5         SNGIEASLLT DPKDVSGRTV DYIIAGGGLV GLTTAAKLTE NPNISVLVIE
F91        SNGIEASLLT DPKDVSGRTV DYIIAGGGLV GLTTAAKLTE NPNISVLVIE
F9         SNGIEASLLT DPKDVSGRTV DYIIAGGGLV GLTTAAKLTE NPNISVLVIE 60         70         80         90        100
wt         SGSYESDRGP IIEDLNAYGD IFGSSVDHAY ETVELATNNQ TALIRSGNGL
parent     SGSYESDRGP IIEDLNAYGD IFGSSVDHAY ETVELATNNQ TALVRSGNGL
A21        SGSYESDRGP IIEDLNAYGD IFGSSVDHAY ETVELATNNQ TALVRSGNGL
A2         SGSYESDRGP IIEDLNAYGD IFGSSVDHAY ETVELATNNQ TALVRSGNGL
F5         SGSYESDRGP IIEDLNAYGD IFGSSVDHAY ETVELATNNQ TALVRSGNGL
F91        SGSYESDRGP IIEDLNAYGD IFGSSVDHAY ETVELATNNQ TALVRSGNGL
F9         SGSYESDRGP IIEDLNAYGD IFGSSVDHAY ETVELATNNQ TALVRSGNGL 110        120        130        140        150
wt         GGSTLVNGGT WTRPHKAQVD SWETVFGNEG WNWDNVAAYS LQAERARAPN
parent     GGSTLVNGGT WTRPHKAQVD SWETVFGNEG WNWDNVAAYS LQAERARAPN
A21        GGSTLVNGGT WTRPHKAQVD SWETVFGNEG WNWDNVAAYS LQAERARAPN
A2         GGSTLVNGGT WTRPHKAQVD SWETVFGNEG WNWDNVAAYS LQAERARAPN
F5         GGSTLVNGGT WTRPHKAQVD SWETVFGNEG WNWDNVAAYS LQAERARAPN
F91        GGSTLINGGT WTRPHKAQVD SWETVFGNEG WNWDNVAAYS LQAERARAPN
F9         GGSTLINGGT WTRPHKAQVD SWETVFGNEG WNWDNVAAYS LQAERARAPN 160        170        180        190        200
wt         AKQIAAGHYF NASCHGVNGT VHAGPRDTGD DYSPIVKALM SAVEDRGVPT
parent     AKQIAAGHYF NTSCHGVNGT VHAGPRDTGD DYSPIVKALM SAVEDRGVPT
A21        AKQIAAGHYF NASCHGVNGT VHAGPRDTGD DYSPIVKALM SAVEDRGVPT
A2         AKQIAAGHYF NTSCHGVNGT VHAGPRDTGD DYSPIVKALM SAVEDRGVPT
F5         AKQIAAGHYF NTSCHGVNGT VHAGPRDTGD DYSPIVKALM SAVEDRGVPT
F91        AKQIAAGHYF NTSCHGVNGT VHAGPRDTGD DYSPIVKALM SAVEDRGVPT
F9         AKQIAAGHYF NTSCHGVNGT VHAGPRDTGD DYSPIVKALM SAVEDRGVPT 210        220        230        240        250
wt         KKDFGCGDPH GVSMFPNTLH EDQVRSDAAR EWLLPNYQRP NLQVLTGQYV
parent     KKDFGCGDPH GVSMFPNTLH EDQVRSDAAR EWLLPNYQRP NLQVLTGQYV
A21        KKDFGCGDPH GVSMFPNTLH EDQVRSDAAR EWLLPNYQRP NLQVLTGQYV
A2         KKDFGCGDPH GVSMFPNTLH EDQVRSDAAR EWLLPNYQRP NLQVLTGQYV
F5         KKDFGCGDPH GVSMFPNTLH EDQVRSDAAR EWLLPNYQRP NLQVLTGQYV
F91        KKDFGCGDPH GVSMFPNTLH EDQVRSDAAR EWLLPNYQRP NLQVLTGQYV
F9         KKDFGCGDPH GVSMFPNTLH EDQVRSDAAR EWLLPNYQRP NLQVLTGQYV 260        270        280        290        300
wt         GKVLLSQNGT TPRAVGVEFG THKGNTHNVY AKHEVLLAAG SAVSPTILEY
parent     GKVLLSQNGT TPRAVGVEFG THKGNTHNVY AKHEVLLAAG SAVSPTILEY
A21        GKVLLSQNGT TPRAVGVEFG THKGNTHNVY AKHEVLLAAG SAVSPTILEY
A2         GKVLLSQNGT TPRAVGVEFG THKGNTHNVY AKHEVLLAAG SAVSPTILEY
```

-continued

```
F5       GKVLLSQNGT TPRAVGVEFG THKGNTHNVY AKHEVLLAAG SAISPTILEY
F91      GKVLLSQNGT TPRAVGVEFG THKGNTHNVY AKHEVLLAAG SAVSPTILEY
F9       GKVLLSQNGT TPRAVGVEFG THKGNTHNVY AKHEVLLAAG SAVSPTILEY

....|....| ....|....| ....|....| ....|....| ....|....|
                    310        320        330        340        350
wt       SGIGMKSILE PLGIDTVVDL PVGLNLQDQT TATVRSRITS AGAGQGQAAW
parent   SGIGMKSILE PLGIDTVVDL PVGLNLQDQT TATVRSRITS AGAGQGQAAW
A21      SGIGMKSILE PLGIDTVVDL PVGLNLQDQT TATVRSRITS AGAGQGQAAW
A2       SGIGMKSILE PLGIDTVVDL PVGLNLQDQT TATVRSRITS AGAGQGQAAW
F5       SGIGMKSILD PLGIDTVVDL PVGLNLQDQT TATVRSRITS AGAGQGQAAW
F91      SGIGMKSILE PLGIDTVVDL PVGLNLQDQT TATVRSRITS AGAGQGQAAW
F9       SGIGMKSILE PLGIDTVVDL PVGLNLQDQT TATVRSRITS AGAGQGQAAW ....|....| ....|....| ....|....| ....|....| ....|....|
                    360        370        380        390        400
wt       FATFNETFGD YSEKAHELLN TKLEQWAEEA VARGGFHNTT ALLIQYENYR
parent   FATFNETFGD YSEKAHELLN TKLEQWAEEA VARGGFHNTT ALLIQYENYR
A21      FATFNETFGD YSEKAHELLN TKLEQWAEEA VARGGFHNTT ALLIQYENYR
A2       FATFNETFGD YSEKAHELLN TKLEQWAEEA VARGGFHNTT ALLIQYENYR
F5       FATFNETFGD YSEKAHELLN TKLEQWAEEA VARGGFHNTT ALLIQYENYR
F91      FATFNETFGD YSEKAHELLN TKLEQWAEEA VARGGFHNTT ALLIQYENYR
F9       FATFNETFGD YSEKAHELLN TKLEQWAEEA VARGGFHNTT ALLIQYENYR ....|....| ....|....| ....|....| ....|....| ....|....|
                    410        420        430        440        450
wt       DWIVNHNVAY SELFLDTAGV ASFDVWDLLP FTRGYVHILD KDPYLHHFAY
parent   DWIVNHNVAY SELFLDTAGV ASFDVWDLLP FTRGYVHILD KDPYLHHFAY
A21      DWIVNHNVAY SELFLDTAGV ASFDVWDLLP FTRGYVHILD KDPYLHHFAY
A2       DWIVNHNVAY SELFLDTAGV ASFDVWDLLP FTRGYVHILD KDPYLHHFAY
F5       DWIVNHNVAY SELFLDTAGV ASFDVWDLLP FTRGYVHILD KDPYLHHFAY
F91      DWIVNHNVAY SELFLDTAGV ASFDVWDLLP FTRGYVHILD KDPYLHHFAY
F9       DWIVNHNVAY SELFLDTAGV ASFDVWDLLP FTRGYVHILD KDPYLHHFAY ....|....| ....|....| ....|....| ....|....| ....|....|
                    460        470        480        490        500
wt       DPQYFLNELD LLGQAAATQL ARNISNSGAM QTYFAGETIP GDNLAYDADL
parent   DPQYFLNELD LLGQAAATQL ARNISNSGAM QTYFAGETIP GDNLAYDADL
A21      DPQYFLNELD LLGQAAATQL ARNISNSGAM QTYFAGETIP GDNLAYDADL
A2       DPQYFLNELD LLGQAAATQL ARNISNSGAM QTYFAGETIP GDNLAYDADL
F5       DPQYFLNELD LLGQAAATQL ARNISNSGAM QTYFAGETIP GDNLAYDADL
F91      DPQYFLNELD LLGQAAATQL ARNISNSGAM QTYFAGETIP GDNLAYDADL
F9       DPQYFLNELD LLGQAAATQL ARNISNSGAM QTYFAGETIP GDNLAYDADL ....|....| ....|....| ....|....| ....|....| ....|....|
                    510        520        530        540        550
wt       SAWTEYIPYH FRPNYHGVGT CSMMPKEMGG VVDNAARVYG VQGLRVIDGS
parent   SAWTEYIPYH FRPNYHGVGT CSMMPKEMGG VVDNAARVYG VQGLRVIDGS
A21      SAWTEYIPYH FRPNYHGVGT CSMMPKEMGG VVDNAAKVYG VQGLRVIDGS
A2       SAWTEYIPYH FRPNYHGVGT CSMMPKEMGG VVDNAAKVYG VQGLRVIDGS
F5       SAWTEYIPYH FRPNYHGVGT CSMMPKEMGG VVDNAAKVYG VQGLRVIDGS
F91      SAWTEYIPYH FRPNYHGVGT CSMMPKEMGG VVDNAARVYG VQGLRVIDGS
F9       SAWTEYIPYH FRPNYHGVGT CSMMPKEMGG VVDNAARVYG VQGLRVIDGS ....|....| ....|....| ....|....| ....
                    560        570        580
wt       IPPTQMSSHV MTVFYAMALK ISDAILEDYA SMQ*
parent   IPPTQMSSHV MTVFYAMALK ISDAILEDYA SMQ*
A21      IPPTQVSSHV MTVFYAMALK ISDAILEDYA SMQ*
A2       IPPTQVSSHV MTVFYAMALK ISDAILEDYA SMQ*
F5       IPPTQVSSHV MTVFYAMALK ISDAILEDYA SMQ*
F91      IPPTQMSSHV MTVFYAMALK ISDAILEDYA SMQ*
F9       IPPTQVSSHV MTVFYAMALK ISDAILEDYA SMQ*
```

METHODS AND EXAMPLES

In the following examples, materials and methods of the present disclosure are provided including the determination of catalytic and stability properties of enzymes obtained by the method. It should be understood that these examples are for illustrative purpose only and are not to be construed as limiting this disclosure in any manner. All publications, patents, and patent applications cited herein are hereby incorporated by reference in their entirety for all purposes.

Example 1

Site-Directed Mutagenesis

The glucose oxidase variants were created using the QuickChange multiple-site-directed mutagenesis kit (Agilent Technologies, USA) and E. coli XL10Gold ultracompetent cells. Site-directed primers (Eurofins MWG Operon, Germany) were synthesized and annealed at different positions in the GOx sequence, which was housed in the pCTCON2 vector and included a c-myc tag.

The PCR mix comprised 400 pg/μL template DNA, 200 nM of the primers, and the remaining components from the mutagenesis kit. The reactions were heated to 95° C. for 1 min, followed by 30 cycles of 95° C. for 1 min, 55° C. for 1 min and 65° C. for 16.5 min, followed by a final extension at 65° C. for 20 min. The reaction products were then digested using DpnI for 3 h at 37° C. and stored at 4° C. until required.

The single stranded DNA obtained from the PCR was introduced into the ultra competent bacteria according to the instructions in the mutagenesis kit and plasmid DNA was isolated using the Macherey-Nagel Plasmid DNA kit (Duren, Germany).

Example 2

Transformation of S. cerevisiae EBY 100 Cells

Plasmid DNA was introduced into S. cerevisiae EBY 100 (as described by Gietz R D and Schiestl R H, Nature protocols 2007, 2: 31-4) using a 2.5-h 42° C. heat shock step. The cells were cultivated in YNB-CAA glucose medium for 48 h at 27° C., 160 rpm, then induced to express GOx by transferring to YNB-CAA Gal/Raf medium under the same conditions for 16-18 h.

Example 3

Agar Plate ABTS Assay

The S. cerevisiae cells were grown at 27° C. for 3 d, replica plated onto YNB-CAA Gal/Raf medium and cultivated for a further 1 d. Analysis medium was prepared by mixing 2% agar with an equal volume of ABTS solution containing 333 mM glucose, 1.75 U/mL HRP and 7 mM ABTS. This was poured over the agar cell plates. Green halos were observed around colonies with GOx activity.

Example 4

MTP ABTS Assay

The S. cerevisiae cells were cultivated (as described in Bulter T et al. In: Directed Enzyme Evolution Screening and Selection Methods, Arnold F H, Georgiou G (eds) Humana Press: Totowa, N. J., 2003) and 5-μL aliquots were transferred to fresh MTPs for the ABTS assay, (as described by Zhu Z et al. Biosensors & Bioelectronics 2006, 21:2046-51; Baron A J et al. J. Biol. Chem. 1994, 269:25095-25105; Sun L et al. Protein Eng Des Select 2001, 14: 699-704) with the following modifications.

The cells were re-suspended in 70 μL PBS and the $OD_{600}$ was determined, then 70 μL ABTS solution was added and the kinetics were measured at 405 nm every 20 s for 10 min. Two measurements were taken from each culture, one using 4 mM ABTS solution containing 250 mM glucose and 1 U/mL HRP, and one with the same components but only 5 mM glucose. Three wild-type clones were included in each microtitre plate for standardization. For each measurement, the slope of the linear region was calculated and normalized to the $OD_{600}$ of the cells in each well.

Example 5

DNA Isolation and Recloning in Pichia pastoris

DNA was extracted from the S. cerevisiae mutants (as described in Singh M V and Weil P A, Analytical Biochemistry 2002, 307:13-17) and the GOx sequence was transferred to the XhoI/XbaI sites of pICZalpha A (Invitrogen, Germany) using the appropriate restriction enzymes (New England Biolabs GmbH, Germany). Competent P. pastoris KM71H cells (Invitrogen, Germany) were prepared and transformed (see Becker D M and Guarente L, Methods Enzymol 1991, 194: 182-187) and the best-performing clone representing each mutant was selected.

Example 6

Protein Purification

After fermentation for 4 d according to Invitrogen recommendations, cells were pelleted by centrifugation at 11,000×g for 10 min using a Beckman Coulter Avanti J26 XP centrifuge (Krefeld Germany). The supernatant was collected and filtered through a 0.22-μm PTFE filter (Carl Roth GmbH, Germany) and the filtrate was concentrated to 5-10 mL using a Viva Flow 50 system with a 10-kDa membrane (Sartorius A G, Germany). The concentrate was dialyzed against 10 mM phosphate buffer (pH 6.0) overnight at 4° C. and loaded onto a 20-mL Fast Flow DEAE Sepharose column (GE Healthcare Europe GmbH, Germany) using the ÄKTApurifier (GE Healthcare Europe GmbH, Germany). The protein was purified using a linear gradient from 10 to 250 mM phosphate buffer pH 6 over 30 column volumes. We tested 50-mL fractions using the ABTS assay and those with separate peaks of GOx activity were collected and concentrated to 5 mL using 10-kDa ultrafiltration columns (Sartorius A G, Germany).

Example 7

Kinetic Analysis Using ABTS Assay

The kinetic characteristics of each GOx variant were determined using triplicate MTP ABTS assays with glucose concentrations ranging from 2.5 to 260 mM, at pH 5.5 and 7.4. The slope of each measurement was calculated over the linear region and fitted onto Michaelis-Menten curves to allow the $K_M$ and $k_{cat}$ values to be determined. Lineweaver-Burk, Eadie-Hofstee and Hanes-Woolf plots were also constructed, and the outliers were identified and removed. The $k_{cat}$ values were determined by measuring absorbance at 280 nm (the absorption of 1.5 mg/mL GOx is considered equivalent to 1 AU based on the sequence, as calculated using ProtParam).

As a control, a parental GOx comprising the amino acid sequence of SEQ ID NO. 3 (with the substitutions at positions corresponding to the amino acid residues T30V, I94V and A162T of the wild-type glucose oxidase from Aspergillus niger (SEQ ID NO: 1)) was used. The nucleic acid encoding the parental GOx is shown in SEQ ID NO: 4.

The kinetic parameters of the enzymes were investigated so that the resulting data could be fitted on the Michaelis-Menten equation. All the GOx mutants had a higher intrinsic activity than the wild type enzyme (tested at pH 5.5) but the difference was more pronounced at pH 7.4. The improved kinetic constants of the mutants are summarized in Table 4. The best performing mutant was A2, with a 1.5-fold lower $K_M$ and a 2.6-fold higher $k_{cat}$, giving an overall four-fold increase in activity at pH 5.5 and a 5.8-fold increase at pH 7.4.

TABLE 4 activity of the mutant enzymes compared to wild type

|  |  | $k_M$ average (mM) | $k_{cat}$ average $s^{-1}$ | Specificity constant $mM^{-1} \cdot s^{-1}$ |
|---|---|---|---|---|
| Wild type | Acetate | 28.26 | 189.38 | 6.70 |
| Parent | buffer | 15.13 | 266.37 | 17.60 |

TABLE 4-continued activity of the mutant enzymes compared to wild type

| Commercial | pH 5.5 | 23.96 | 376.03 | 15.68 |
|---|---|---|---|---|
| A2 | | 18.93 | 578.32 | 30.55 |
| A21 | | 15.75 | 466.18 | 29.59 |
| F5 | | 16.05 | 368.16 | 22.93 |
| F9 | | 13.05 | 350.97 | 26.88 |
| F91 | | 15.06 | 321.53 | 21.34 |

| | | $k_M$ average (mM) | $k_{cat}$ average $s^{-1}$ | Specificity constant $mM^{-1} \cdot s^{-1}$ |
|---|---|---|---|---|
| wt | PBS | 23.19 | 130.16 | 5.61 |
| parent | buffer | 14.71 | 227.99 | 15.49 |
| commercial | pH 7.4 | 18.86 | 372.01 | 19.72 |
| A2 | | 13.08 | 432.17 | 33.11 |
| A21 | | 10.93 | 350.77 | 32.09 |
| F5 | | 14.26 | 308.44 | 21.62 |
| F9 | | 10.37 | 228.36 | 22.02 |
| F91 | | 9.53 | 266.80 | 27.99 |

As mentioned above, all the selected mutants had a higher intrinsic activity than the wild type enzyme (tested at pH 5.5) but the difference was more pronounced at pH 7.4. The best mutant (A2) was fourfold more active at pH 5.5 and 5.8-fold more active at pH 7.4 suggesting it would be ideal for the development of miniature biofuel cells intended to operate in humans.

FIG. 1 shows the kinetic constants determined by using the ABTS assay in 150 µL of reaction volume with a 0.5 cm light pathway using PBS buffer pH 7.4, 1 U/mL HRP and 4 mM ABTS. The glucose concentrations were varied from 2.5 to 260 mM. The kinetics were measured at 405 nm every 20 s for 10 min. The slope of each measurement was calculated over the linear region. The data were fitted using Origin 8 (OriginLab Corporation, Northampton) on Michaelis-Menten curves and the $K_M$ and $k_{cat}$ were determined.

Figure 2:
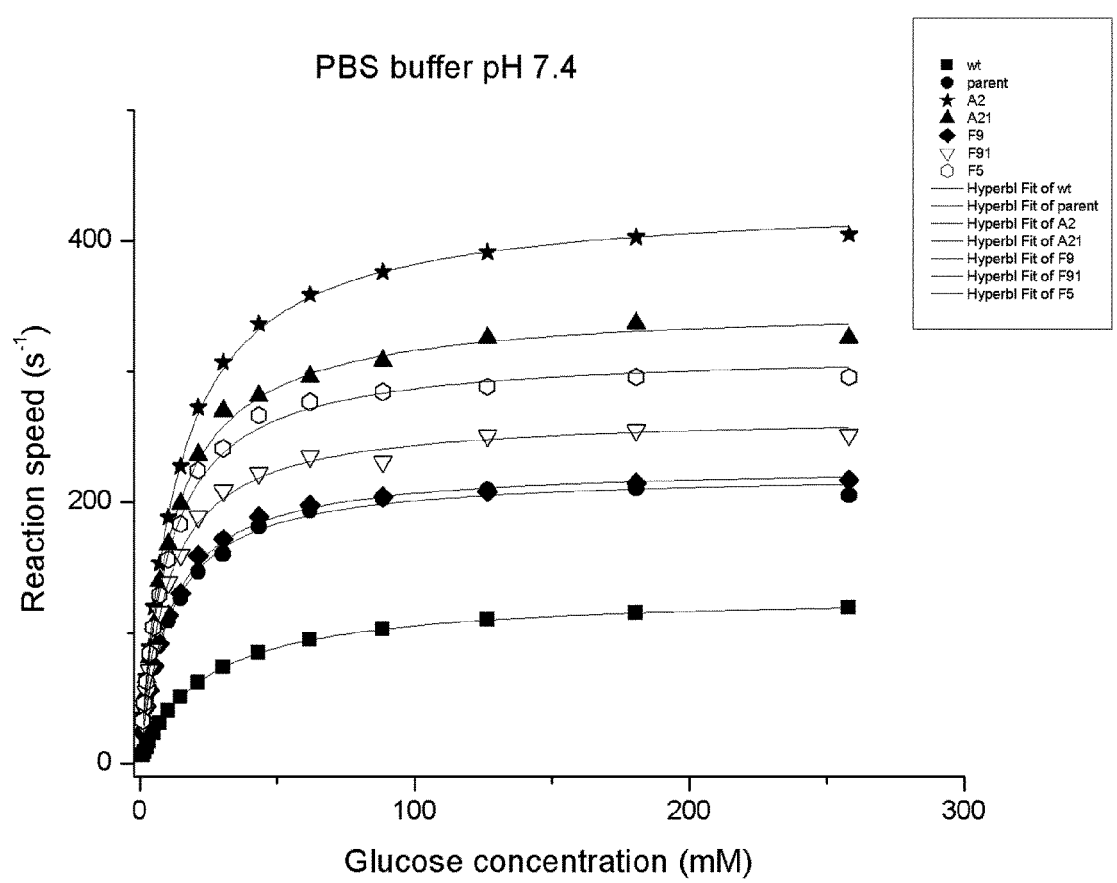
FIG. 2 is a diagram showing the enzyme kinetics of GOx variants according to the present disclosure at pH 7.4.

FIG. 2 shows the kinetic constants determined by using the ABTS assay in a 150 µL reaction volume with a 0.5 cm light pathway using 50 mM sodium acetate buffer pH 5.5, 1 U/mL HRP and 4 mM ABTS. The glucose concentrations were varied from 2.5 to 260 mM. The kinetics were measured at 405 nm every 20 s for 10 min. The slope of each measurement was calculated over the linear region. The data were fitted using Origin 8 (OriginLab Corporation, Northampton) on Michaelis-Menten curves and the $K_M$ and $k_{cat}$ were determined.

Example 8

Kinetic Analysis Using Ferrocenemethanol

Ferrocenemethanol (oxidized) was prepared as described by Zhu et al. and the pH adjusted to the corresponding pH used for activity measurements using 1 M KOH or 1 M HCl. Purified glucose oxidase variants were used for determining $K_M$ and $k_{cat}$ for ferrocenemethanol in the presence of oxygen. Each measurement was performed in MTP in triplicate using 400 mM Glucose and varying concentrations of ferrocenmethanol ox ranging from 0.22-10 mM. The measurements were performed at pH 5.5, 7.4 and 8. The reaction kinetics were monitored at 625 nm. Using these measurements, the $K_M$ and $k_{cat}$ were determined by fitting the Michaelis-Menten model on the data using non-linear regression by the least squares method. In order to calculate the kcat, the enzyme concentration was measured by absorbance at 280 nm (the absorption of 1.5 mg/mL GOx is considered equivalent to 1 AU based on the sequence, as calculated using ProtParam).

The outliers were identified and removed. The kinetic parameters for ferrocenmethanol are summarized in Table 5.

As the $k_{cat}$ is comparable between the pH values tested for an individual mutant but the $K_M$ is much lower at high pH values, the specificity constant greatly improves for high pH values. The $K_M$ values of the mutants and the wild type are comparable for each pH value, thus showing that the increased affinity of the mutants towards glucose did not negatively affect the affinity to ferrocenemethanol. In the presence of oxygen, the mediator is still able to compete with oxygen.

TABLE 5

Activity of the mutant enzymes compared to wild type using Ferrocenmethanol as a substrate

| | | $k_M$ average (mM) | $k_{cat}$ average $s^{-1}$ | Specificity constant $mM^{-1} \cdot s^{-1}$ |
|---|---|---|---|---|
| Wild type | Acetate | 3.40 | 84.36 | 24.81 |
| A2 | buffer | 2.80 | 686.71 | 245.37 |
| A21 | pH 5.5 | 1.89 | 523.43 | 276.46 |
| F5 | | 3.00 | 555.72 | 185.20 |
| F9 | | 2.82 | 322.49 | 114.54 |
| F91 | | 2.89 | 357.05 | 123.54 |

| | | $k_M$ average (mM) | $k_{cat}$ average $s^{-1}$ | Specificity constant $mM^{-1} \cdot s^{-1}$ |
|---|---|---|---|---|
| wt | PBS | 0.32 | 67.00 | 210.07 |
| A2 | buffer | 0.31 | 593.02 | 1889.12 |
| A21 | pH 7.4 | 0.31 | 551.05 | 1756.20 |
| F5 | | 0.33 | 464.38 | 1419.29 |
| F9 | | 0.34 | 300.09 | 887.09 |
| F91 | | 0.30 | 316.60 | 1065.02 |

| | | $k_M$ average (mM) | $k_{cat}$ average $s^{-1}$ | Specificity constant $mM^{-1} \cdot s^{-1}$ |
|---|---|---|---|---|
| wt | PBS | 0.27 | 67.72 | 255.27 |
| A2 | buffer | 0.34 | 698.61 | 2027.18 |
| A21 | pH 8.0 | 0.31 | 635.71 | 2045.65 |
| F5 | | 0.23 | 535.91 | 2311.04 |
| F9 | | 0.25 | 335.07 | 1353.19 |
| F91 | | 0.25 | 324.74 | 1320.48 |

All mutants show higher activity for the mediator compared with the wild type variant. Mutant A 2 is still the best mutant with up to 10 times improved activity for ferrocenmethanol.

Example 9

Kinetic Analysis Using
N,N-Dimethyl-p-Nitrosoaniline (NDMA)

N,N-dimethyl-p-nitrosoaniline (NDMA) solution was prepared by adding the chemical in the appropriate buffer (phosphate buffer pH 7.4 or acetate buffer pH 5.5). This oxidizied N,N-dimethyl-p-nitrosoaniline was used for kinetic measurements with the previously purified GOx mutants. For this, the reaction speed of GOx with the mediators was determined for varying mediator concentrations. NDMA reduction was monitored at 528 nm at saturating glucose concentration. Determination of $K_M$ and $k_{cat}$ was done using 400 mM glucose and varying the concentration of NDMA between 0.46 to 15.33 mM, at pH 5.5 and 7.4. All measurements were performed in triplicate in MTPs. The obtained kinetic data for NDMA at pH 5.5 and 7.4 were fitted on Michaelis-Menten curves. As a quality control and for the identification and remove of outliers, the Lineweaver-Burk, Hanes-Woolf and Eadie-Hofstee curves were plotted as well. The kinetic data for NDMA are presented in Table 6.

TABLE 6

Activity of the mutant enzymes compared to wild type using N,N-dimethyl-p-nitrosoaniline as a substrate

|  |  | $k_M$ average (mM) | $k_{cat}$ average $s^{-1}$ | Specificity constant $mM^{-1} \cdot s^{-1}$ |
|---|---|---|---|---|
| Wild type | Acetate | 12.16 | 19.10 | 1.57 |
| A2 | buffer | 21.75 | 300.66 | 13.83 |
| A21 | pH 5.5 | 21.81 | 228.86 | 10.49 |
| F5 |  | 27.75 | 240.29 | 8.66 |
| F9 |  | 21.18 | 255.96 | 12.08 |
| F91 |  | 12.12 | 97.11 | 8.01 |

|  |  | $k_M$ average (mM) | $k_{cat}$ average $s^{-1}$ | Specificity constant $mM^{-1} \cdot s^{-1}$ |
|---|---|---|---|---|
| wt | PBS | 9.05 | 10.71 | 1.18 |
| A2 | buffer | 13.24 | 118.25 | 8.93 |
| A21 | pH 7.4 | 10.86 | 103.56 | 9.53 |
| F5 |  | 14.41 | 122.97 | 8.54 |
| F9 |  | 12.84 | 139.72 | 10.88 |
| F91 |  | 9.83 | 62.55 | 6.36 |

As it was the case for FM, NDMA can compete with oxygen for the wild type enzyme as well as the mutants. The affinity towards the mediator is also increased at higher pH which is indicated by lower KM values. The wild type enzyme and F91 show lower KM values than the other variants at both pH tested, indicating that the mutation M556V, which is not present in F91 and the wild type enzyme but in all other variants, increases the KM value. This was not observed for FM. The specificity constant for the mutants increased in a range of 5 times (F91) to 8 times (A2) compared to the wild type enzyme.

Example 10

Thermal Stability

The thermal stability of GOx mutants was determined by incubating the enzyme in 50 mM acetate buffer (pH 5.5) at 60° C. in the absence of substrate (see Bhatti H N, Saleem N, Food Technol. Biotechnol. 47 (3) 331-335, 2009, 47: 331-335) and measuring the residual activity of periodic aliquots using the ABTS assay. A(t) values, representing the percentage residual activity, were plotted at different time points relative to 100% activity at time 0, on an exponential equation to determine the inactivation rate constants (kd) as shown below:

$$A(t) = e^{-kd*t}$$

The half times for thermal stability were calculated by considering A(t) equivalent to 0.5 A(0).

According to the present disclosure the thermal stability of all the GOx mutants was greater than the wild type enzyme (see Table 5). In this case, the best-performing mutant was F9-1 with a half-life at 60° C. that was twice as long as the wild type enzyme.

TABLE 7 thermal stability of the mutant enzymes compared to wild type

|  | $t_{1/2}$ (min) |
|---|---|
| Parent | 9.00 |
| Wild type | 10.50 |
| A2 | 11.74 |
| A21 | 13.86 |
| F5 | 11.74 |
| F9 | 15.75 |
| F91 | 19.80 |

REFERENCES (1) M Rossi, L.; D Quach, A.; Rosenzweig, Z. *Analytical and Bioanalytical Chemistry* 2004, 380, 606-613.
(2) Wong, C. M.; Wong, K. H.; Chen, X. D. *Applied microbiology and biotechnology* 2008, 78, 927-38.
(3) Bankar, S. B.; Bute, M. V.; Singhal, R. S., Ananthanarayan, L. *Biotechnology advances* 2009, 27, 489-501.
(4) Mano, N.; Mao, F.; Heller, A. *Journal of American Chemical Society* 2002, 124, 12962-12963.
(5) Mano, N.; Mao, F.; Heller, A. *Chembiochem: a European journal of chemical biology* 2004, 5, 1703-1705.
(6) Mano, N.; Heller, A. *Journal of Electrochemical Society* 2003, 150, 1136-1138.
(7) Heller, A. *Phys. Chem. Chem. Phys.* 2004, 6, 209-216.
(8) Arnold, F. H.; Volkov, A. A. *Current opinion in chemical biology* 1999, 3, 54-9.
(9) Tawfik, D. S.; Griffiths, A. D. *Nature biotechnology* 1998, 16, 652-6.
(10) Bernath, K.; Hai, M.; Mastrobattista, E.; Griffiths, A. D.; Magdassi, S.; Tawfik, D. S. *Analytical biochemistry* 2004, 325, 151-7.
(11) Schaerli, Y.; Holifelder, F. *Molecular bioSystems* 2009, 5, 1392-404.
(12) Prodanovic, R.; Ostafe, R.; Blanusa, M.; Schwaneberg, U. *Analytical and Bioanalytical Chemistry* 2011, in review.
(13) Aharoni, A.; Amitai, G.; Bernath, K.; Magdassi, S.; Tawfik, D. S. *Chemistry & biology* 2005, 12, 1281-9.
(14) Mastrobattista, E.; Taly, V.; Chanudet, E.; Treacy, P.; Kelly, B. T.; Griffiths, A. D. *Chemistry & biology* 2005, 12, 1291-300.
(15) Lipovsek, D.; Antipov, E.; Armstrong, K. a; Olsen, M. J.; Klibanov, A. M.; Tidor, B.; Wittrup, K. D. *Chemistry & biology* 2007, 14, 1176-85.
(16) Prodanovic, R.; Ostafe, R.; Scacioc, A.; Schwaneberg, U. *Combinatorial chemistry & high throughput screening* 2011, 14, 55-60.
(17) Amitai, G.; Gupta, R. D.; Tawfik, D. S. *HFSP Journal* 2007, 1, 67.
(18) van Gijlswijk, R. P.; Zijlmans, H. J.; Wiegant, J.; Bobrow, M. N.; Erickson, T. J.; Adler, K. E.; Tanke, H. J.; Raap, A. K. *The journal of histochemistry and cytochemistry: official journal of the Histochemistry Society* 1997, 45, 375-82.
(19) Gietz, R. D.; Schiestl, R. H. *Nature protocols* 2007, 2, 31-4.
(20) Gai, S. A.; Wittrup, K. D. *Current opinion in structural biology* 2007, 17, 467-73.
(21) Bulter, T.; Sieber, V.; Alcalde, M. In *Directed Enzyme Evolution Screening and Selection Methods*; Arnold, F. H.; Georgiou, G., Eds.; Humana Press: Totowa, N. J., 2003.

(22) Zhu, Z.; Momeu, C.; Zakhartsev, M.; Schwaneberg, U. *Biosensors & bioelectronics* 2006, 21, 2046-51.
(23) Baron, A. J.; Stevens, C.; Wilmot, C.; Seneviratne, K. D.; Blakeley, V.; Dooley, D. M.; Phillips, S. E.; Knowles, P. F.; McPherson, M. J. *J. Biol. Chem.* 1994, 269, 25095-25105.
(24) Sun, L.; Petrounia, I. P.; Yagasaki, M.; Bandara, G.; Arnold, F. H. *Protein Engineering Design and Selection* 2001, 14, 699-704.
(25) Singh, M. V.; Weil, P. A. *Analytical biochemistry* 2002, 307, 13-7.
(26) Becker, D. M.; Guarente, L. *Methods in enzymology* 1991, 194, 182-7.
(27) Bhatti, H. N.; Saleem, N. Food Technol. Biotechnol. 47 (3) 331-335, 2009, 47, 331-335.

What is claimed is:

1. A polypeptide having improved thermal stability and at the same time improved glucose oxidase activity as compared to wild-type glucose oxidase from *Aspergillus niger* (SEQ ID NO: 1), wherein said polypeptide comprises variations at positions corresponding to the amino acid residues T30 and I94 in the wild-type glucose oxidase from *Aspergillus niger* (SEQ ID NO: 1), and at least one or more further variations at positions corresponding to amino acid residues A162, M556, R537, R37, and V106, and wherein the amino acid sequence of said polypeptide has at least 80% sequence identity to the amino acid sequence of SEQ ID NO: 1.

2. The polypeptide according to claim 1, wherein said polypeptide comprises at least one or more variations at positions corresponding to amino acid residues V293 or E310.

3. The polypeptide according to claim 1, wherein said variations are substitutions selected from the group consisting of T30V, I94V, R37K, V106I, A162T, V293I, E310D, R537K, M556V, and a combination thereof.

4. The polypeptide according to claim 1, wherein said polypeptide comprises the substitutions selected from the group consisting of:
   a) M556V, R537K, T30V, I94V;
   b) M556V, R537K, T30V, I94V, A162T;
   c) M556V, R537K, R37K, V293I, E310D, V106I, T30V, I94V, A162T;
   d) M556V, R37K, V106I, T30V, I94V, A162T; and
   e) R37K, V106I, T30V, I94V, A162T.

5. The polypeptide according to claim 1, wherein said polypeptide comprises an amino acid sequence selected from the group consisting of SEQ ID NO: 5, SEQ ID NO: 7, SEQ ID NO: 9, SEQ ID NO: 11 and SEQ ID NO: 13.

6. The polypeptide according to claim 1, wherein said polypeptide comprises the amino acid sequence of SEQ ID NO: 7.

7. The polypeptide according to claim 1, wherein said polypeptide comprises the amino acid sequence of SEQ ID NO: 11.

8. The polypeptide according to claim 1, wherein the amino acid sequence has at least a minimum percentage sequence identity of at least 85%, at least 90%, at least 93%, at least 96%, at least 97%, at least 98% or at least 99% to the amino acid sequence of SEQ ID NO: 1.

9. A composition comprising the polypeptide according to claim 1, wherein the composition is selected from the group consisting of a food composition, a pharmaceutical composition, a diagnostic composition or a cosmetic composition.

10. A method for assaying glucose in a sample, comprising contacting the sample with the polypeptide having glucose oxidase activity according to claim 1, and measuring the amount of the glucose oxidized by the glucose oxidase.

11. A device for assaying glucose in a sample comprising the polypeptide having glucose oxidase activity according to claim 1 and an electron mediator.

* * * * *

SEQUENCE LISTING

```
<160> NUMBER OF SEQ ID NOS: 14

<210> SEQ ID NO 1
<211> LENGTH: 583
<212> TYPE: PRT
<213> ORGANISM: Aspergillus niger
<220> FEATURE:
<223> OTHER INFORMATION: wild-type

<400> SEQUENCE: 1

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Thr Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300
```

Met Lys Ser Ile Leu Glu Pro Leu Gly Ile Asp Thr Val Val Asp Leu
305                 310                 315                 320

Pro Val Gly Leu Asn Leu Gln Asp Gln Thr Ala Thr Val Arg Ser
            325                 330                 335

Arg Ile Thr Ser Ala Gly Ala Gly Gln Gly Gln Ala Ala Trp Phe Ala
                340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
                420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
            565                 570                 575

Glu Asp Tyr Ala Ser Met Gln
            580

<210> SEQ ID NO 2
<211> LENGTH: 1752
<212> TYPE: DNA
<213> ORGANISM: Aspergillus niger
<220> FEATURE:
<221> NAME/KEY: source
<222> LOCATION: 1..1752
<223> OTHER INFORMATION: /organism="Aspergillus niger"
    /note="wild-type"
    /mol_type="unassigned DNA"

<400> SEQUENCE: 2
agcaatggca ttgaagccag cctcctgact gatcccaagg atgtctccgg ccgcacggtc    60
gactacatca tcgctggtgg aggtctgact ggactcacca ccgctgctcg tctgacggag   120
aaccccaaca tcagtgtgct cgtcatcgaa agtggctcct acgagtcgga cagaggtcct   180
atcattgagg acctgaacgc ctacggcgac atctttggca gcagtgtaga ccacgcctac   240
gagaccgtgg agctcgctac caacaatcaa accgcgctga tccgctccgg aaatggtctc   300

```
ggtggctcta ctctagtgaa tggtggcacc tggactcgcc cccacaaggc acaggttgac    360
tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacgcatcct gccatggtgt taatggtact gtccatgccg accccgcga caccggcgat    540 gactattctc ccatcgtcaa ggctctcatg agcgctgtcg aagaccgggg cgttcccacc    600
aagaaagact tcggatgcgg tgaccccat ggtgtgtcca tgttccccaa caccttgcac    660
gaagaccaag tgcgctccga tgccgctcgc gaatggctac ttcccaacta ccaacgtccc    720
aacctgcaag tcctgaccgg acagtatgtt ggtaaggtgc tccttagcca gaacggcacc    780 accctcgtg ccgttggcgt ggaattcggc acccacaagg gcaacaccca acgtttac    840 gctaagcacg aggtcctcct ggccgcgggc tccgctgtct ctcccacaat cctcgaatat    900
tccggtatcg aatgaagtc catcctggag ccccttggta tcgacaccgt cgttgacctg    960
cccgtcggct tgaacctgca ggaccagacc accgctaccg tccgctcccg catcacctct   1020
gctggtgcag gacagggaca ggccgcttgg ttcgccacct tcaacgagac ctttggtgac   1080
tattccgaaa aggcacacga gctgctcaac accaagctgg agcagtgggc cgaagaggcc   1140
gtcgcccgtg gcggattcca caacaccacc gccttgctca tccagtacga gaactaccgc   1200
gactggattg tcaaccacaa cgtcgcgtac tcggaactct tcctcgacac tgccggagta   1260
gccagcttcg atgtgtggga ccttctgccc ttcacccgag atacgttca catcctcgac   1320 aaggaccct accttcacca cttcgcctac gaccctcagt acttcctcaa cgagctggac   1380
ctgctcggtc aggctgccgc tactcaactg gcccgcaaca tctccaactc cggtgccatg   1440
cagacctact cgctgggga gactatcccc ggtgataacc tcgcgtatga tgccgatttg   1500
agcgcctgga ctgagtacat cccgtaccac ttccgtccta actaccatgg cgtgggtact   1560
tgctccatga tgccgaagga gatgggcggt gttgttgata atgctgcccg tgtgtatggt   1620
gtgcagggac tgcgtgtcat tgatggttct attcctccta cgcaaatgtc gtcccatgtc   1680
atgacggtgt tctatgccat ggcgctaaaa atttcggatg ctatcttgga agattatgct   1740
tccatgcagt ga                                                       1752
```

<210> SEQ ID NO 3
<211> LENGTH: 583
<212> TYPE: PRT
<213> ORGANISM: Artificial Sequence
<220> FEATURE:
<223> OTHER INFORMATION: Parent GOx Variant

<400> SEQUENCE: 3

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Val Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Val Asn Gly Gly Thr Trp Thr
```

```
            100                 105                 110
Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
            130                 135                 140

Arg Ala Arg Ala Pro Asn Ala Lys Gln Ile Ala Ala Gly His Tyr Phe
145                 150                 155                 160

Asn Thr Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
                180                 185                 190

Val Glu Asp Arg Gly Val Pro Thr Lys Lys Asp Phe Gly Cys Gly Asp
                195                 200                 205

Pro His Gly Val Ser Met Phe Pro Asn Thr Leu His Glu Asp Gln Val
                210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
                260                 265                 270

Lys Gly Asn Thr His Asn Val Tyr Ala Lys His Glu Val Leu Leu Ala
                275                 280                 285

Ala Gly Ser Ala Val Ser Pro Thr Ile Leu Glu Tyr Ser Gly Ile Gly
                290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
                340                 345                 350

Thr Phe Asn Glu Thr Phe Gly Asp Tyr Ser Glu Lys Ala His Glu Leu
                355                 360                 365

Leu Asn Thr Lys Leu Glu Gln Trp Ala Glu Glu Ala Val Ala Arg Gly
                370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
                420                 425                 430

Arg Gly Tyr Val His Ile Leu Asp Lys Asp Pro Tyr Leu His His Phe
                435                 440                 445

Ala Tyr Asp Pro Gln Tyr Phe Leu Asn Glu Leu Asp Leu Leu Gly Gln
450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
                500                 505                 510

Pro Asn Tyr His Gly Val Gly Thr Cys Ser Met Met Pro Lys Glu Met
                515                 520                 525
```

```
Gly Gly Val Val Asp Asn Ala Ala Arg Val Tyr Gly Val Gln Gly Leu
        530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 4
<211> LENGTH: 1752
<212> TYPE: DNA
<213> ORGANISM: Artificial Sequence
<220> FEATURE:
<221> NAME/KEY: source
<222> LOCATION: 1..1752
<223> OTHER INFORMATION: /organism="Artificial Sequence"
      /note="Parent GOx Variant"
      /mol_type="unassigned DNA"

<400> SEQUENCE: 4
agcaatggca ttgaagccag cctcctgact gatcccaagg atgtctccgg ccgcacggtc      60
gactacatca tcgctggtgg aggtctggtt ggactcacca ccgctgctcg tctgacggag     120
aaccccaaca tcagtgtgct cgtcatcgaa agtggctcct acgagtcgga cagaggtcct     180
atcattgagg acctgaacgc ctacggcgac atctttggca gcagtgtaga ccacgcctac     240
gagaccgtgg agctcgctac caacaatcaa accgcgctgg tccgctccgg aaatggtctc     300
ggtggctcta ctctagtgaa tggtggcacc tggactcgcc ccacaaggc acaggttgac      360 tcttgggaga ctgtctttgg aaatgagggc tggaactggg acaatgtggc cgcctactcc     420
ctccaggctg agcgtgctcg cgcaccaaat gccaaacaga tcgctgctgg ccactacttc     480
aacacatcct gccatggtgt taatggtact gtccatgccg accccgcga caccggcgat      540 gactattctc ccatcgtcaa agctctcatg agcgctgtcg aagaccgggg cgttcccacc     600
aagaaagact tcggatgcgg tgaccccat ggtgtgtcca tgttcccaa caccttgcac       660 gaagaccaag tgcgctccga tgccgctcgc gaatggctac ttcccaacta ccaacgtccc     720
aacctgcaag tcctgaccgg acagtatgtt ggtaaggtgc tccttagcca gaacggcacc     780 accctcgtg ccgttggcgt ggaattcggc acccacaagg gcaacaccca aacgttttac      840
gctaagcacg aggtcctcct ggccgcgggc tccgctgtct ctcccacaat cctcgaatat     900
tccggtatcg gaatgaagtc catcctggag ccccttggta tcgacaccgt cgttgacctg     960
cccgtcggct tgaacctgca ggaccagacc accgctaccg tccgctcccg catcacctct    1020
gctggtgcag acaggggaca ggccgcttgg ttcgccacct tcaacgagac ctttggtgac    1080
tattccgaaa aggcacacga gctgctcaac accaagctgg agcagtgggc cgaagaggcc    1140
gtcgcccgtg gcggattcca caacaccacc gccttgctca tccagtacga gaactaccgc    1200
gactggattg tcaaccacaa cgtcgcgtac tcggaactct tcctcgacac tgccggagta    1260
gccagcttcg atgtgtggga ccttctgccc ttcacccgag gatacgttca catcctcgac    1320 aaggaccccct accttcacca cttcgcctac gaccctcagt acttcctcaa cgagctggac    1380
ctgctcggtc aggctgccgc tactcaactg gcccgcaaca tctccaactc cggtgccatg    1440
cagacctact cgctgggga gactatcccc ggtgataacc tcgcgtatga tgccgatttg    1500
agcgcctgga ctgagtacat cccgtaccac ttccgtccta actaccatgg cgtgggtact    1560
```

-continued

```
tgctccatga tgccgaagga gatgggcggt gttgttgata atgctgcccg tgtgtatggt    1620
gtgcagggac tgcgtgtcat tgatggttct attcctccta cgcaaatgtc gtcccatgtc    1680
atgacggtgt tctatgccat ggcgctaaaa atttcggatg ctatcttgga agattatgct    1740
tccatgcagt ga                                                         1752

<210> SEQ ID NO 5
<211> LENGTH: 583
<212> TYPE: PRT
<213> ORGANISM: Artificial Sequence
<220> FEATURE:
<223> OTHER INFORMATION: GOx Variant A21

<400> SEQUENCE: 5

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
```

```
                    325                 330                 335
Arg Ile Thr Ser Ala Gly Ala Gly Gln Gly Gln Ala Ala Trp Phe Ala
                340                 345                 350
Thr Phe Asn Glu Thr Phe Gly Asp Tyr Ser Glu Lys Ala His Glu Leu
            355                 360                 365
Leu Asn Thr Lys Leu Glu Gln Trp Ala Glu Glu Ala Val Ala Arg Gly
        370                 375                 380
Gly Phe His Asn Thr Thr Ala Leu Leu Ile Gln Tyr Glu Asn Tyr Arg
385                 390                 395                 400
Asp Trp Ile Val Asn His Asn Val Ala Tyr Ser Glu Leu Phe Leu Asp
                405                 410                 415
Thr Ala Gly Val Ala Ser Phe Asp Val Trp Asp Leu Leu Pro Phe Thr
                420                 425                 430
Arg Gly Tyr Val His Ile Leu Asp Lys Asp Pro Tyr Leu His His Phe
            435                 440                 445
Ala Tyr Asp Pro Gln Tyr Phe Leu Asn Glu Leu Asp Leu Leu Gly Gln
        450                 455                 460
Ala Ala Thr Gln Leu Ala Arg Asn Ile Ser Asn Ser Gly Ala Met
465                 470                 475                 480
Gln Thr Tyr Phe Ala Gly Glu Thr Ile Pro Gly Asp Asn Leu Ala Tyr
                485                 490                 495
Asp Ala Asp Leu Ser Ala Trp Thr Glu Tyr Ile Pro Tyr His Phe Arg
            500                 505                 510
Pro Asn Tyr His Gly Val Gly Thr Cys Ser Met Met Pro Lys Glu Met
        515                 520                 525
Gly Gly Val Val Asp Asn Ala Ala Lys Val Tyr Gly Val Gln Gly Leu
        530                 535                 540
Arg Val Ile Asp Gly Ser Ile Pro Pro Thr Gln Val Ser Ser His Val
545                 550                 555                 560
Met Thr Val Phe Tyr Ala Met Ala Leu Lys Ile Ser Asp Ala Ile Leu
                565                 570                 575
Glu Asp Tyr Ala Ser Met Gln
            580

<210> SEQ ID NO 6
<211> LENGTH: 1752
<212> TYPE: DNA
<213> ORGANISM: Artificial Sequence
<220> FEATURE:
<221> NAME/KEY: source
<222> LOCATION: 1..1752
<223> OTHER INFORMATION: /organism="Artificial Sequence"
      /note="GOx Variant A21"
      /mol_type="unassigned DNA"

<400> SEQUENCE: 6
agcaatggca ttgaagccag cctcctgact gatcccaagg atgtctccgg ccgcacggtc    60
gactacatca tcgctggtgg aggtctggtt ggactcacca ccgctgctcg tctgacggag   120
aaccccaaca tcagtgtgct cgtcatcgaa gtggctcct acgagtcgga cagaggtcct    180
atcattgagg acctgaacgc ctacggcgac atctttggca gcagtgtaga ccacgcctac   240
gagaccgtgg agctcgctac caacaatcaa accgcgctgg tccgctccgg aaatggtctc   300
ggtggctcta ctctagtgaa tggtggcacc tggactcgcc ccacaaggc acaggttgac    360 tcttgggaga ctgtctttgg aaatgagggc tggaactggg acaatgtggc cgcctactcc   420
ctccaggctg agcgtgctcg cgcaccaaat gccaaacaga tcgctgctgg ccactacttc   480
```

```
aacgcatcct gccatggtgt taatggtact gtccatgccg accccgcga caccggcgat    540
gactattctc ccatcgtcaa ggctctcatg agcgctgtcg aagaccgggg cgttcccacc    600
aagaaagact tcggatgcgg tgacccccat ggtgtgtcca tgttccccaa caccttgcac    660
gaagaccaag tgcgctccga tgccgctcgc gaatggctac ttcccaacta ccaacgtccc    720
aacctgcaag tcctgaccgg acagtatgtt ggtaaggtgc tccttagcca gaacggcacc    780
accccctcgtg ccgttggcgt ggaattcggc acccacaagg caacaccca caacgtttac    840
gctaagcacg aggtcctcct ggccgcgggc tccgctgtct ctcccacaat cctcgaatat    900
tccggtatcg gaatgaagtc catcctggag ccccttggta tcgacaccgt cgttgacctg    960
cccgtcggct tgaacctgca ggaccagacc accgctaccg tccgctcccg catcacctct   1020
gctggtgcag acagggaca gccgcttgg ttcgccacct tcaacgagac ctttggtgac   1080
tattccgaaa aggcacacga gctgctcaac accaagctgg agcagtgggc cgaagaggcc   1140
gtcgcccgtg gcggattcca caacaccacc gccttgctca tccagtacga gaactaccgc   1200
gactggattg tcaaccacaa cgtcgcgtac tcggaactct tcctcgacac tgccggagta   1260
gccagcttcg atgtgtggga ccttctgccc ttcacccgag gatacgttca catcctcgac   1320
aaggacccct accttcacca cttcgcctac gacccctcagt acttcctcaa cgagctggac   1380
ctgctcggtc aggctgccgc tactcaactg gcccgcaaca tctccaactc cggtgccatg   1440
cagacctact cgctgggga gactatcccc ggtgataacc tcgcgtatga tgccgatttg   1500
agcgcctgga ctgagtacat cccgtaccac ttccgtccta actaccatgg cgtgggtact   1560
tgctccatga tgccgaagga gatgggcggt gttgttgata atgctgccaa agtgtatggt   1620
gtgcagggac tgcgtgtcat tgatggttct attcctccta cgcaagtttc gtcccatgtc   1680
atgacggtgt tctatgccat ggcgctaaaa atttcggatg ctatcttgga agattatgct   1740
tccatgcagt ga                                                        1752
```

<210> SEQ ID NO 7
<211> LENGTH: 583
<212> TYPE: PRT
<213> ORGANISM: Artificial Sequence
<220> FEATURE:
<223> OTHER INFORMATION: GOx Variant A2

<400> SEQUENCE: 7

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125
```

```
Glu Gly Trp Asn Trp Asp Asn Val Ala Ala Tyr Ser Leu Gln Ala Glu
    130                 135                 140
Arg Ala Arg Ala Pro Asn Ala Lys Gln Ile Ala Ala Gly His Tyr Phe
145                 150                 155                 160
Asn Thr Ser Cys His Gly Val Asn Gly Thr Val His Ala Gly Pro Arg
                165                 170                 175
Asp Thr Gly Asp Asp Tyr Ser Pro Ile Val Lys Ala Leu Met Ser Ala
            180                 185                 190
Val Glu Asp Arg Gly Val Pro Thr Lys Lys Asp Phe Gly Cys Gly Asp
        195                 200                 205
Pro His Gly Val Ser Met Phe Pro Asn Thr Leu His Glu Asp Gln Val
    210                 215                 220
Arg Ser Asp Ala Ala Arg Glu Trp Leu Leu Pro Asn Tyr Gln Arg Pro
225                 230                 235                 240
Asn Leu Gln Val Leu Thr Gly Gln Tyr Val Gly Lys Val Leu Leu Ser
                245                 250                 255
Gln Asn Gly Thr Thr Pro Arg Ala Val Gly Val Glu Phe Gly Thr His
            260                 265                 270
Lys Gly Asn Thr His Asn Val Tyr Ala Lys His Glu Val Leu Leu Ala
        275                 280                 285
Ala Gly Ser Ala Val Ser Pro Thr Ile Leu Glu Tyr Ser Gly Ile Gly
    290                 295                 300
Met Lys Ser Ile Leu Glu Pro Leu Gly Ile Asp Thr Val Val Asp Leu
305                 310                 315                 320
Pro Val Gly Leu Asn Leu Gln Asp Gln Thr Thr Ala Thr Val Arg Ser
                325                 330                 335
Arg Ile Thr Ser Ala Gly Ala Gly Gln Gly Gln Ala Ala Trp Phe Ala
            340                 345                 350
Thr Phe Asn Glu Thr Phe Gly Asp Tyr Ser Glu Lys Ala His Glu Leu
        355                 360                 365
Leu Asn Thr Lys Leu Glu Gln Trp Ala Glu Ala Val Ala Arg Gly
    370                 375                 380
Gly Phe His Asn Thr Thr Ala Leu Leu Ile Gln Tyr Glu Asn Tyr Arg
385                 390                 395                 400
Asp Trp Ile Val Asn His Asn Val Ala Tyr Ser Glu Leu Phe Leu Asp
                405                 410                 415
Thr Ala Gly Val Ala Ser Phe Asp Val Trp Asp Leu Leu Pro Phe Thr
            420                 425                 430
Arg Gly Tyr Val His Ile Leu Asp Lys Asp Pro Tyr Leu His His Phe
        435                 440                 445
Ala Tyr Asp Pro Gln Tyr Phe Leu Asn Glu Leu Asp Leu Leu Gly Gln
    450                 455                 460
Ala Ala Ala Thr Gln Leu Ala Arg Asn Ile Ser Asn Ser Gly Ala Met
465                 470                 475                 480
Gln Thr Tyr Phe Ala Gly Glu Thr Ile Pro Gly Asp Asn Leu Ala Tyr
                485                 490                 495
Asp Ala Asp Leu Ser Ala Trp Thr Glu Tyr Ile Pro Tyr His Phe Arg
            500                 505                 510
Pro Asn Tyr His Gly Val Gly Thr Cys Ser Met Met Pro Lys Glu Met
        515                 520                 525
Gly Gly Val Val Asp Asn Ala Ala Lys Val Tyr Gly Val Gln Gly Leu
    530                 535                 540
Arg Val Ile Asp Gly Ser Ile Pro Pro Thr Gln Val Ser Ser His Val
```

```
                545                 550                 555                 560
Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 8
<211> LENGTH: 1752
<212> TYPE: DNA
<213> ORGANISM: Artificial Sequence
<220> FEATURE:
<221> NAME/KEY: source
<222> LOCATION: 1..1752
<223> OTHER INFORMATION: /organism="Artificial Sequence"
      /note="GOx Variant A2"
      /mol_type="unassigned DNA"

<400> SEQUENCE: 8
agcaatggca ttgaagccag cctcctgact gatcccaagg atgtctccgg ccgcacggtc     60
gactacatca tcgctggtgg aggtctggtt ggactcacca ccgctgctcg tctgacggag    120
aaccccaaca tcagtgtgct cgtcatcgaa agtggctcct acgagtcgga cagaggtcct    180
atcattgagg acctgaacgc ctacggcgac atctttggca gcagtgtaga ccacgcctac    240
gagaccgtgg agctcgctac caacaatcaa accgcgctgg tccgctccgg aaatggtctc    300
ggtggctcta ctctagtgaa tggtggcacc tggactcgcc cccacaaggc acaggttgac    360
tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacacatcct gccatggtgt aatggtact gtccatgccg accccgcga caccggcgat    540 gactattctc ccatcgtcaa ggctctcatg agcgctgtcg aagaccgggg cgttcccacc    600
aagaaagact tcggatgcgg tgaccccat ggtgtgtcca tgttcccaa caccttgcac    660 gaagaccaag tgcgctccga tgccgctcgc gaatggctac ttcccaacta ccaacgtccc    720
aacctgcaag tcctgaccgg acagtatgtt ggtaaggtgc ccttagcca gaacggcacc    780 acccctcgtg ccgttggcgt ggaattcggc acccacaagg caacaccca caacgtttac    840 gctaagcacg aggtcctcct ggccgcgggc tccgctgtct ctcccacaat cctcgaatat    900
tccggtatcg gaatgaagtc catcctggag ccccttggta tcgacaccgt cgttgacctg    960
cccgtcggct tgaacctgca ggaccagacc accgctaccg tccgctcccg catcacctct   1020
gctggtgcag acagggaca ggccgcttgg ttcgccacct tcaacgagac ctttggtgac   1080
tattccgaaa aggcacacga gctgctcaac accaagctgg agcagtgggc cgaagaggcc   1140
gtcgcccgtg gcggattcca caacaccacc gccttgctca tccagtacga gaactaccgc   1200
gactggattg tcaaccacaa cgtcgcgtac tcggaactct tcctcgacac tgccggagta   1260
gccagcttcg atgtgtggga ccttctgccc ttcacccgag atacgttca catcctcgac   1320 aaggacccct accttcacca cttcgcctac gacccctcagt acttcctcaa cgagctggac   1380
ctgctcggtc aggctgccgc tactcaactg gcccgcaaca tctccaactc cggtgccatg   1440
cagacctact cgctgggga gactatcccc ggtgataacc tcgcgtatga tgccgatttg   1500
agcgcctgga ctgagtacat cccgtaccac ttccgtccta actaccatgg cgtgggtact   1560
tgctccatga tgccgaagga gatgggcggt gttgttgata tgctgccaa agtgtatggt   1620 gtgcagggac tgcgtgtcat tgatggttct attcctccta cgcaagtttc gtcccatgtc   1680
atgacggtgt tctatgccat ggcgctaaaa atttcggatg ctatcttgga agattatgct   1740
```
tccatgcagt ga 1752

<210> SEQ ID NO 9
<211> LENGTH: 583
<212> TYPE: PRT
<213> ORGANISM: Artificial Sequence
<220> FEATURE:
<223> OTHER INFORMATION: GOx Variant F5

<400> SEQUENCE: 9

```
Ser Asn Gly Ile Glu Ala Ser Leu Leu Thr Asp Pro Lys Asp Val Ser
1               5                   10                  15
Gly Arg Thr Val Asp Tyr Ile Ile Ala Gly Gly Leu Val Gly Leu
            20                  25                  30
Thr Thr Ala Ala Lys Leu Thr Glu Asn Pro Asn Ile Ser Val Leu Val
        35                  40                  45
Ile Glu Ser Gly Ser Tyr Glu Ser Asp Arg Gly Pro Ile Ile Glu Asp
    50                  55                  60
Leu Asn Ala Tyr Gly Asp Ile Phe Gly Ser Ser Val Asp His Ala Tyr
65                  70                  75                  80
Glu Thr Val Glu Leu Ala Thr Asn Asn Gln Thr Ala Leu Val Arg Ser
                85                  90                  95
Gly Asn Gly Leu Gly Gly Ser Thr Leu Val Asn Gly Gly Thr Trp Thr
            100                 105                 110
Arg Pro His Lys Ala Gln Val Asp Ser Trp Glu Thr Val Phe Gly Asn
        115                 120                 125
Glu Gly Trp Asn Trp Asp Asn Val Ala Ala Tyr Ser Leu Gln Ala Glu
    130                 135                 140
Arg Ala Arg Ala Pro Asn Ala Lys Gln Ile Ala Ala Gly His Tyr Phe
145                 150                 155                 160
Asn Thr Ser Cys His Gly Val Asn Gly Thr Val His Ala Gly Pro Arg
                165                 170                 175
Asp Thr Gly Asp Asp Tyr Ser Pro Ile Val Lys Ala Leu Met Ser Ala
            180                 185                 190
Val Glu Asp Arg Gly Val Pro Thr Lys Lys Asp Phe Gly Cys Gly Asp
        195                 200                 205
Pro His Gly Val Ser Met Phe Pro Asn Thr Leu His Glu Asp Gln Val
    210                 215                 220
Arg Ser Asp Ala Ala Arg Glu Trp Leu Leu Pro Asn Tyr Gln Arg Pro
225                 230                 235                 240
Asn Leu Gln Val Leu Thr Gly Gln Tyr Val Gly Lys Val Leu Leu Ser
                245                 250                 255
Gln Asn Gly Thr Thr Pro Arg Ala Val Gly Val Glu Phe Gly Thr His
            260                 265                 270
Lys Gly Asn Thr His Asn Val Tyr Ala Lys His Glu Val Leu Leu Ala
        275                 280                 285
Ala Gly Ser Ala Ile Ser Pro Thr Ile Leu Glu Tyr Ser Gly Ile Gly
    290                 295                 300
Met Lys Ser Ile Leu Asp Pro Leu Gly Ile Asp Thr Val Val Asp Leu
305                 310                 315                 320
Pro Val Gly Leu Asn Leu Gln Asp Gln Thr Thr Ala Thr Val Arg Ser
                325                 330                 335
Arg Ile Thr Ser Ala Gly Ala Gly Gln Gly Gln Ala Ala Trp Phe Ala
            340                 345                 350
```

```
Thr Phe Asn Glu Thr Phe Gly Asp Tyr Ser Glu Lys Ala His Glu Leu
                355                 360                 365
Leu Asn Thr Lys Leu Glu Gln Trp Ala Glu Ala Val Ala Arg Gly
    370                 375                 380
Gly Phe His Asn Thr Thr Ala Leu Leu Ile Gln Tyr Glu Asn Tyr Arg
385                 390                 395                 400
Asp Trp Ile Val Asn His Asn Val Ala Tyr Ser Glu Leu Phe Leu Asp
                405                 410                 415
Thr Ala Gly Val Ala Ser Phe Asp Val Trp Asp Leu Leu Pro Phe Thr
                420                 425                 430
Arg Gly Tyr Val His Ile Leu Asp Lys Asp Pro Tyr Leu His His Phe
                435                 440                 445
Ala Tyr Asp Pro Gln Tyr Phe Leu Asn Glu Leu Asp Leu Leu Gly Gln
                450                 455                 460
Ala Ala Ala Thr Gln Leu Ala Arg Asn Ile Ser Asn Ser Gly Ala Met
465                 470                 475                 480
Gln Thr Tyr Phe Ala Gly Glu Thr Ile Pro Gly Asp Asn Leu Ala Tyr
                485                 490                 495
Asp Ala Asp Leu Ser Ala Trp Thr Glu Tyr Ile Pro Tyr His Phe Arg
                500                 505                 510
Pro Asn Tyr His Gly Val Gly Thr Cys Ser Met Met Pro Lys Glu Met
                515                 520                 525
Gly Gly Val Val Asp Asn Ala Ala Lys Val Tyr Gly Val Gln Gly Leu
                530                 535                 540
Arg Val Ile Asp Gly Ser Ile Pro Pro Thr Gln Val Ser Ser His Val
545                 550                 555                 560
Met Thr Val Phe Tyr Ala Met Ala Leu Lys Ile Ser Asp Ala Ile Leu
                565                 570                 575
Glu Asp Tyr Ala Ser Met Gln
                580

<210> SEQ ID NO 10
<211> LENGTH: 1752
<212> TYPE: DNA
<213> ORGANISM: Artificial Sequence
<220> FEATURE:
<221> NAME/KEY: source
<222> LOCATION: 1..1752
<223> OTHER INFORMATION: /organism="Artificial Sequence"
      /note="GOx Variant F5"
      /mol_type="unassigned DNA"

<400> SEQUENCE: 10
agcaatggca ttgaagccag cctcctgact gatcccaagg atgtctccgg ccgcacggtc     60
gactacatca tcgctggtgg aggtctggtt ggactcacca ccgctgctaa actgacggag    120
aaccccaaca tcagtgtgct cgtcatcgaa agtggctcct acgagtcgga cagaggtcct    180
atcattgagg acctgaacgc ctacggcgac atctttggca gcagtgtaga ccacgcctac    240
gagaccgtgg agctcgctac caacaatcaa accgcgctgg tccgctccgg aaatggtctc    300
ggtggctcta ctctagtgaa tggtggcacc tggactcgcc cccacaaggc acaggttgac    360
tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacacatcct gccatggtgt taatggtact gtccatgccg accccgcga caccggcgat    540 gactattctc ccatcgtcaa ggctctcatg agcgctgtcg aagaccgggg cgttcccacc    600
```

```
aagaaagact tcggatgcgg tgaccccat ggtgtgtcca tgttcccaa caccttgcac    660 gaagaccaag tgcgctccga tgccgctcgc gaatggctac ttcccaacta ccaacgtccc    720
aacctgcaag tcctgaccgg acagtatgtt ggtaaggtgc tccttagcca gaacggcacc    780
acccctcgtg ccgttggcgt ggaattcggc acccacaagg gcaacaccca caacgtttac    840
gctaagcacg aggtcctcct ggccgcgggc tccgctattt ctcccacaat cctcgaatat    900
tccggtatcg gaatgaagtc catcctggat ccccttggta tcgacaccgt cgttgacctg    960
cccgtcggct tgaacctgca ggaccagacc accgctaccg tccgctcccg catcacctct   1020
gctggtgcag acagggaca ggccgcttgg ttcgccacct tcaacgagac ctttggtgac   1080
tattccgaaa aggcacacga gctgctcaac accaagctgg agcagtgggc cgaagaggcc   1140
gtcgcccgtg gcggattcca acaccaccg ccttgctca tccagtacga aactaccgc      1200 gactggattg tcaaccacaa cgtcgcgtac tcggaactct tcctcgacac tgccggagta   1260
gccagcttcg atgtgtggga ccttctgccc ttcacccgag atacgttca catcctcgac    1320 aaggacccct accttcacca cttcgcctac gaccctcagt acttcctcaa cgagctggac   1380
ctgctcggtc aggctgccgc tactcaactg gcccgcaaca tctccaactc cggtgccatg   1440
cagacctact cgctgggga gactatcccc ggtgataacc tcgcgtatga tgccgatttg    1500
agcgcctgga ctgagtacat cccgtaccac ttccgtccta actaccatgg cgtgggtact   1560
tgctccatga tgccgaagga gatgggcggt gttgttgata atgctgccaa agtgtatggt   1620 gtgcaggac tgcgtgtcat tgatggttct attcctccta cgcaagtttc gtcccatgtc     1680
atgacggtgt tctatgccat ggcgctaaaa atttcggatg ctatcttgga agattatgct    1740
tccatgcagt ga                                                                                                       1752

<210> SEQ ID NO 11
<211> LENGTH: 583
<212> TYPE: PRT
<213> ORGANISM: Artificial Sequence
<220> FEATURE:
<223> OTHER INFORMATION: GOx Variant F91

<400> SEQUENCE: 11

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Lys Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Ile Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160
```

```
Asn Thr Ser Cys His Gly Val Asn Gly Thr Val His Ala Gly Pro Arg
            165                 170                 175

Asp Thr Gly Asp Asp Tyr Ser Pro Ile Val Lys Ala Leu Met Ser Ala
        180                 185                 190

Val Glu Asp Arg Gly Val Pro Thr Lys Lys Asp Phe Gly Cys Gly Asp
    195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
            245                 250                 255

Gln Asn Gly Thr Thr Pro Arg Ala Val Gly Val Glu Phe Gly Thr His
        260                 265                 270

Lys Gly Asn Thr His Asn Val Tyr Ala Lys His Glu Val Leu Leu Ala
    275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Asp Thr Val Asp Leu
305                 310                 315                 320

Pro Val Gly Leu Asn Leu Gln Asp Gln Thr Thr Ala Thr Val Arg Ser
            325                 330                 335

Arg Ile Thr Ser Ala Gly Ala Gly Gln Gly Gln Ala Ala Trp Phe Ala
        340                 345                 350

Thr Phe Asn Glu Thr Phe Gly Asp Tyr Ser Glu Lys Ala His Glu Leu
    355                 360                 365

Leu Asn Thr Lys Leu Glu Gln Trp Ala Glu Gly Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
            405                 410                 415

Thr Ala Gly Val Ala Ser Phe Asp Val Trp Asp Leu Pro Phe Thr
        420                 425                 430

Arg Gly Tyr Val His Ile Leu Asp Lys Asp Pro Tyr Leu His His Phe
    435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Ser Ala Trp Thr Glu Tyr Ile Pro Tyr His Phe Arg
        500                 505                 510

Pro Asn Tyr His Gly Val Gly Thr Cys Ser Met Met Pro Lys Glu Met
    515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
            565                 570                 575
```

Glu Asp Tyr Ala Ser Met Gln
         580

<210> SEQ ID NO 12
<211> LENGTH: 1752
<212> TYPE: DNA
<213> ORGANISM: Artificial Sequence
<220> FEATURE:
<221> NAME/KEY: source
<222> LOCATION: 1..1752
<223> OTHER INFORMATION: /organism="Artificial Sequence"
      /note="GOx Variant F91"
      /mol_type="unassigned DNA"

<400> SEQUENCE: 12

| | | |
|---|---|---|
| agcaatggca ttgaagccag cctcctgact gatcccaagg atgtctccgg ccgcacggtc | 60 |
| gactacatca tcgctggtgg aggtctggtt ggactcacca ccgctgctaa actgacggag | 120 |
| aaccccaaca tcagtgtgct cgtcatcgaa agtggctcct acgagtcgga cagaggtcct | 180 |
| atcattgagg acctgaacgc ctacggcgac atctttggca gcagtgtaga ccacgcctac | 240 |
| gagaccgtgg agctcgctac caacaatcaa accgcgctgg tccgctccgg aaatggtctc | 300 |
| ggtggctcta ctctaattaa tggtggcacc tggactcgcc cccacaaggc acaggttgac | 360 |
| tcttgggaga ctgtctttgg aaatgagggc tggaactggg acaatgtggc cgcctactcc | 420 |
| ctccaggctg agcgtgctcg cgcaccaaat gccaaacaga tcgctgctgg ccactacttc | 480 |
| aacacatcct gccatggtgt aatggtact gtccatgccg accccgcga caccggcgat | 540 |
| gactattctc ccatcgtcaa ggctctcatg agcgctgtcg aagaccgggg cgttcccacc | 600 |
| aagaaagact cggatgcgg tgacccccat ggtgtgtcca tgttcccaa caccttgcac | 660 |
| gaagaccaag tgcgctccga tgccgctcgc gaatggctac ttcccaacta ccaacgtccc | 720 |
| aacctgcaag tcctgaccgg acagtatgtt ggtaaggtgc tccttagcca gaacggcacc | 780 |
| accctcgtg ccgttggcgt ggaattcggc acccacaagg gcaacaccca caacgtttac | 840 |
| gctaagcacg aggtcctcct ggccgcgggc tccgctgtct ctccacaat cctcgaatat | 900 |
| tccggtatcg gaatgaagtc catcctggag ccccttggta tcgacaccgt cgttgacctg | 960 |
| cccgtcggct tgaacctgca ggaccagacc accgctaccg tccgctcccg catcacctct | 1020 |
| gctggtgcag acaggggaca ggccgcttgg ttcgccacct tcaacgagac ctttggtgac | 1080 |
| tattccgaaa aggcacacga gctgctcaac accaagctgg agcagtgggc cgaagaggcc | 1140 |
| gtcgcccgtg gcggattcca caacaccacc gccttgctca tccagtacga gaactaccgc | 1200 |
| gactggattg tcaaccacaa cgtcgcgtac tcggaactct tcctcgacac tgccggagta | 1260 |
| gccagcttcg atgtgtggga ccttctgccc ttcacccgag atacgttca tcctcgac | 1320 |
| aaggacccct accttcacca cttcgcctac gaccctcagt acttcctcaa cgagctggac | 1380 |
| ctgctcggtc aggctgccgc tactcaactg gcccgcaaca tctccaactc cggtgccatg | 1440 |
| cagacctact cgctgggga gactatcccc ggtgataacc tcgcgtatga tgccgatttg | 1500 |
| agcgcctgga ctgagtacat cccgtaccac ttccgtccta actaccatgg cgtgggtact | 1560 |
| tgctccatga tgccgaagga gatgggcggt gttgttgata tgctgcccg tgtgtatggt | 1620 |
| gtgcagggac tgcgtgtcat tgatggttct attcctccta cgcaaatgtc gtcccatgtc | 1680 |
| atgacggtgt tctatgccat ggcgctaaaa attcggatg ctatcttgga agattatgct | 1740 |
| tccatgcagt ga | 1752 |

<210> SEQ ID NO 13
<211> LENGTH: 583
<212> TYPE: PRT
<213> ORGANISM: Artificial Sequence
<220> FEATURE:
<223> OTHER INFORMATION: GOx Variant F9

<400> SEQUENCE: 13

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Lys Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Ile Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Thr Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365
```

Leu Asn Thr Lys Leu Glu Gln Trp Ala Glu Glu Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
                420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
                500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Val Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 14
<211> LENGTH: 1752
<212> TYPE: DNA
<213> ORGANISM: Artificial Sequence
<220> FEATURE:
<221> NAME/KEY: source
<222> LOCATION: 1..1752
<223> OTHER INFORMATION: /organism="Artificial Sequence"
    /note="GOx Variant F9"
    /mol_type="unassigned DNA"

<400> SEQUENCE: 14
agcaatggca ttgaagccag cctcctgact gatcccaagg atgtctccgg ccgcacggtc    60
gactacatca tcgctggtgg aggtctggtt ggactcacca ccgctgctaa actgacggag   120
aaccccaaca tcagtgtgct cgtcatcgaa agtggctcct acgagtcgga cagaggtcct   180
atcattgagg acctgaacgc ctacggcgac atctttggca gcagtgtaga ccacgcctac   240
gagaccgtgg agctcgctac caacaatcaa accgcgctgg tccgctccgg aaatggtctc   300
ggtggctcta ctctaattaa tggtggcacc tggactcgcc cccacaaggc acaggttgac   360
tcttgggaga ctgtctttgg aaatgagggc tggaactggg acaatgtggc cgcctactcc   420
ctccaggctg agcgtgctcg cgcaccaaat gccaaacaga tcgctgctgg ccactacttc   480
aacacatcct gccatggtgt taatggtact gtccatgccg accccgcga caccggcgat   540 gactattctc ccatcgtcaa ggctctcatg agcgctgtcg aagaccgggg cgttcccacc   600
aagaaagact tcggatgcgg tgacccccat ggtgtgtcca tgttccccaa caccttgcac   660

```
gaagaccaag tgcgctccga tgccgctcgc gaatggctac ttcccaacta ccaacgtccc      720
aacctgcaag tcctgaccgg acagtatgtt ggtaaggtgc tccttagcca gaacggcacc      780
acccctcgtg ccgttggcgt ggaattcggc acccacaagg gcaacaccca caacgtttac      840
gctaagcacg aggtcctcct ggccgcgggc tccgctgtct ctcccacaat cctcgaatat      900
tccggtatcg gaatgaagtc catcctggag ccccttggta tcgacaccgt cgttgacctg      960
cccgtcggct tgaacctgca ggaccagacc accgctaccg tccgctcccg catcacctct     1020
gctggtgcag gacagggaca ggccgcttgg ttcgccacct caacgagac ctttggtgac      1080 tattccgaaa aggcacacga gctgctcaac accaagctgg agcagtgggc cgaagaggcc     1140
gtcgcccgtg gcggattcca caacaccacc gccttgctca tccagtacga gaactaccgc     1200
gactggattg tcaaccacaa cgtcgcgtac tcggaactct tcctcgacac tgccggagta     1260
gccagcttcg atgtgtggga ccttctgccc ttcacccgag gatacgttca catcctcgac     1320
aaggacccct accttcacca cttcgcctac gaccctcagt acttcctcaa cgagctggac     1380
ctgctcggtc aggctgccgc tactcaactg gcccgcaaca tctccaactc cggtgccatg     1440
cagacctact tcgctgggga gactatcccc ggtgataacc tcgcgtatga tgccgatttg     1500
agcgcctgga ctgagtacat cccgtaccac ttccgtccta actaccatgg cgtgggtact     1560
tgctccatga tgccgaagga gatgggcggt gttgttgata atgctgcccg tgtgtatggt     1620
gtgcagggac tgcgtgtcat tgatggttct attcctccta cgcaagtttc gtcccatgtc     1680
atgacggtgt tctatgccat ggcgctaaaa atttcggatg ctatcttgga agattatgct     1740
tccatgcagt ga                                                         1752
```